United States Patent [19]
Komoriya et al.

[11] Patent Number: 5,714,342
[45] Date of Patent: Feb. 3, 1998

[54] COMPOSITIONS FOR THE DETECTION OF PROTEASE IN BIOLOGICAL SAMPLES AND METHODS OF USE THEREFO

[75] Inventors: Akira Komoriya; Beverly S. Packard, both of Rockville, Md.

[73] Assignee: OncoImmunin, Inc., Kensington, Md.

[21] Appl. No.: 549,008

[22] Filed: Oct. 27, 1995

Related U.S. Application Data

[63] Continuation-in-part of Ser. No. 331,383, Oct. 28, 1994, Pat. No. 5,605,809.

[51] Int. Cl.[6] .................. C12Q 1/37; C12Q 1/00; C09K 11/06; C07D 311/88
[52] U.S. Cl. .................. 435/23; 435/24; 435/4; 435/195; 435/212; 435/218; 435/219; 435/968; 252/301.16; 252/646; 549/227; 549/283
[58] Field of Search .................. 435/23, 24, 4, 435/195, 212, 218, 219, 968; 252/301.16, 646; 549/227, 283

[56] References Cited

U.S. PATENT DOCUMENTS

| | | | |
|---|---|---|---|
| 4,557,862 | 12/1985 | Mangel et al. | 435/23 |
| 4,648,893 | 3/1987 | Roux | 435/23 |
| 4,708,929 | 11/1987 | Henderson | 435/7.5 |
| 4,780,421 | 10/1988 | Kameda et al. | 435/518 |
| 4,897,444 | 1/1990 | Brynes et al. | 435/23 |
| 5,212,298 | 5/1993 | Rademacher et al. | 435/7.92 |

OTHER PUBLICATIONS

Carmel, A. et al. *FEBS Letters*, 30.11 (1973) month not available.
Knight, C.G. et al. *FEBS* 10610, 296:263 (1992) month not available.
Latt, S.A. et al. *Analytical Biochemistry* 50:56 (1972) month not available.
Matayoshi, E.D. et al. *Science*, 247: (1990) month not available.
Nagase, H. et al. *The Journal of Biological Chemistry* 269:20952 (1994) month not available.
Wang, G.T. et al. *Tetrahedron Letters* 31:6493 (1990) month not available.
Wu, P. et al. *Analytical Biochemistry* 218:1 (1994) month not available.

*Primary Examiner*—Louise Leary
*Attorney, Agent, or Firm*—Townsend and Townsend and Crew LLP

[57] ABSTRACT

The present invention provides for novel reagents whose fluorescence increases in the presence of particular proteases. The reagents comprise a characteristically folded peptide backbone each end of which is conjugated to a fluorophore. When the folded peptide is cleaved, as by digestion with a protease, the fluorophores provide a high intensity fluorescent signal at a visible wavelength. Because of their high fluorescence signal in the visible wavelengths, these protease indicators are particularly well suited for detection of protease activity in biological samples, in particular in frozen tissue sections. Thus this invention also provides for methods of detecting protease activity in situ in frozen sections.

45 Claims, 4 Drawing Sheets

COMPOSITIONS FOR THE DETECTION OF PROTEASE IN BIOLOGICAL SAMPLES AND METHODS OF USE THEREFO

CROSS-REFERENCE TO RELATED APPLICATIONS

This is a continuation-in-part of patent application U.S. Ser. No. 08/331,383, filed on Oct. 28, 1994 now U.S. Pat. No. 5,605,809, issued on Feb. 25, 1997, which is herein incorporated by reference for all purposes.

FIELD OF THE INVENTION

This invention pertains to a class of novel fluorogenic compositions whose fluorescence level increases in the presence active proteases. These fluorogenic protease indicators typically fluoresce at visible wavelengths and are thus highly useful for the detection and localization of protease activity in biological samples.

BACKGROUND OF THE INVENTION

Proteases represent a number of families of proteolytic enzymes that catalytically hydrolyze peptide bonds. Principal groups of proteases include metalloproteases, serine proteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and can be characterized by alterations in the activity of specific proteases and their inhibitors. For example emphysema, arthritis, thrombosis, cancer metastasis and some forms of hemophilia result from the lack of regulation of serine protease activities (see, for example, *Textbook of Biochemistry with Clinical Correlations*, John Wiley and Sons, Inc. New York (1993)). Similarly, proteases have been implicated in cancer metastasis. Increased synthesis of the protease urokinase has been correlated with an increased ability to metastasize in many cancers. Urokinase activates plasmin from plasminogen which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. *Adv. Cancer. Res.*, 44:139 (1985).

Clearly measurement of changes in the activity of specific proteases is clinically significant in the treatment and management of the underlying disease states. Proteases, however, are not easy to assay. Typical approaches include ELISA using antibodies that bind the protease or RIA using various labeled substrates. With their natural substrates assays are difficult to perform and expensive. With currently available synthetic substrates the assays are expensive, insensitive and nonselective. In addition, many "indicator" substrates require high quantities of protease which results, in part, in the self destruction of the protease.

Recent approaches to protease detection rely on a cleavage-induced spectroscopic change in a departing chromogen or fluorogen located in the P1' position (the amino acid position on the carboxyl side of the cleavable peptide bond) (see, for example U.S. Pat. Nos. 4,557,862 and 4,648,893). However, many proteases require two or three amino acid residues on either side of the scissile bond for recognition of the protease and thus, these approaches lack protease specificity.

Recently however, fluorogenic indicator compositions have been developed in which a "donor" fluorophore is joined to an "acceptor" chromophore by a short bridge containing a (7 amino acid) peptide that is the binding site for an HIV protease and linkers joining the fluorophore and chromophore to the peptide (Wang et al. *Tetra. Letts.* 45:6493–6496 (1990)). The signal of the donor fluorophore was quenched by the acceptor chromophore through a process believed to involve resonance energy transfer (RET). Cleavage of the peptide resulted in separation of the chromophore and fluorophore, removal of the quench and a subsequent signal was measured from the donor fluorophore.

Unfortunately, the design of the bridge between the donor and the acceptor led to relatively inefficient quenching limiting the sensitivity of the assay. In addition, the chromophore absorbed light in the ultraviolet range reducing the sensitivity for detection in biological samples which typically contain molecules that absorb strongly in the ultraviolet.

Clearly fluorogenic protease indicators that show a high signal level when cleaved, and a very low signal level when intact, that show a high degree of protease specificity, and that operate exclusively in the visible range thereby rendering them suitable for use in biological samples are desirable. The compositions of the present invention provide these and other benefits.

SUMMARY OF THE INVENTION

The present invention provides for novel reagents whose fluorescence increases in the presence of particular proteases. These fluorogenic protease indicators provide a high intensity fluorescent signal at a visible wavelength when they are digested by a protease. Because of their high fluorescence signal in the visible wavelengths, these protease indicators are particularly well suited for detection of protease activity in biological samples, in particular, in frozen tissue sections.

The fluorogenic protease indicators of the present invention are compositions suitable for detection of the activity of a protease. These compositions have the general formula:

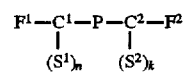

in which P is a peptide comprising a protease binding site for said protease consisting of about 2 to about 8, more preferably about 2 to about 6 and most preferably about 2 to about 4 amino acids; $F^1$ and $F^2$ are fluorophores; $S^1$ and $S^2$ are peptide spacers ranging in length from 1 to about 50 amino acids; n and k are independently 0 or 1; and $C^1$ and $C^2$ are conformation determining regions comprising peptides ranging in length from about 1 to about 3 amino acids. The conformation determining regions each introduce a bend into the composition thereby creating a generally U-shaped configuration of the composition in which the fluorophores are adjacent to each other with a separation of less than about 100 Å. When either of the spacers ($S^1$ and $S^2$) are present they are linked to the protease binding site by a peptide bond to the alpha carbon of the terminal amino acid. Thus, when n is 1, $S^1$ is joined to $C^1$ by a peptide bond through a terminal alpha amino group of $C^1$, and when k is 1, $S^2$ is joined to $C^2$ by a peptide bond through a terminal alpha carboxyl group of $C^2$.

The amino acid residues comprising a protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

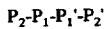

$$P_2\text{-}P_1\text{-}P_1'\text{-}P_2'$$

and the protease would cleave the binding region between $P_1$ and $P_1'$.

In a preferred embodiment, protease binding site (P) is a tetrapeptide, $C^1$ is a tripeptide and $C^2$ is an amino acid or a dipeptide. The composition thus has the formula:

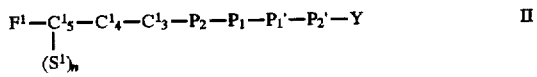

$$F^1-\underset{(S^1)_n}{\underset{|}{C^1_5}}-C^1_4-C^1_3-P_2-P_1-P_1'-P_2'-Y \qquad \text{II}$$

where $C^1_5$, $C^1_4$, $C^1_3$, $P_1$, $P_1'$, $P_2'$ are amino acids, and Y is a composition selected from the group consisting of compounds of formulas:

$$C^2_3-\underset{(S^2)_k}{\underset{|}{C^2_4}}-F^2 \qquad \text{III}$$

and $$\underset{(S^2)_k}{\underset{|}{C^2_3}}-F^2 \qquad \text{IV}$$

where $C^2_3$, $C^2_3$ are amino acids (note the subscripts are numbered relative to the cleavage site).

In a particularly preferred embodiment, the composition is a composition of formula II in which the amino acid composition of P corresponds to the 4 amino acids symmetrically disposed adjacent to the cleavage site (the $P_1$-$P_1'$ peptide bond) cut by a particular protease. The conformation determining regions are thus designed by first determining the protease binding region, determining the "left-over" residues that would lie in the conformation determining regions, and if necessary, modifying those residues according to the following guidelines:

1. If the $P_2'$ site is not a Pro then $C^2$ is a dipeptide (Formula III) Pro-Cys, Aib-Cys, Pro-Lys, or Aib-Lys, while conversely, if the $P_2'$ site is a Pro then $C^2$ is a single amino acid residue (Formula IV) Cys or Lys.
2. If the $P_2$ site is not a Pro then $C^1$ is a tripepride consisting of Asp-$C^1_4$-Pro, Asp-$C^1_4$-Aib, Asp-Aib-Pro, Asp-Pro-$C^1_3$, Asp-Aib-$C^1_3$, Asp-Pro-Aib, or Asp-Aib-Aib, while if the $P_2$ site is a Pro residue then group $C^1$ is a tripeptide consisting of Asp-$C^1_4$-$C^1_3$ or Asp-$C^1_4$-Aib.
3. If the $P_3$ ($C^1_3$) residue is a Pro then $C^1$ is a tripeptide consisting of Asp-$C^1_4$-Pro or Asp-Aib-Pro.
4. If the $P_4$ ($C^1_4$) residue is a Pro then $C^1$ is a tripeptide consisting of Asp-Pro-$C^1_3$ or Asp-Pro-Aib.
5. If $P_2$ and $C^1_3$ are both not prolines then $C^1$is a tripeptide consisting of Asp-Pro-$C^1_3$, Asp-Aib-$C^1_3$, AsP-$C^1_4$-Pro, AsP-$C^1_4$-*Aib*, Asp-Pro-Aib, or Asp-Aib-Pro.

Table 2 indicates particularly preferred protease binding sites (P) and suitable conformation determining regions ($C^1$ and $C^2$). Thus, this invention also includes compositions of formula II in which $P_2$ is Pro, Gly, Phe, Arg, Leu, Gln, Glu, His, Ile, or Ala; $P_1$ is Cys, Met, Nle, Arg, Leu, Gly, His, Glu, Ala, Phe, Tyr, or Asn; $P_1'$ is Thr, Ser, Met, Nle, Leu, Ala, Ile, Phe, Val, Glu, His, or Tyr; and $P_2'$ is Ile, Gly, Met, Nle, Leu, Ala, Gln, Arg, Val, Ser, Tyr, Gln, or Asn. Particularly preferred are compositions of formula II in which the P domain ($P_2$-$P_1$-$P_1'$-$P_2'$) is Pro-Met-Ser-Ile (SEQ ID NO:1), Pro-Nle-Ser-Ile (SEQ ID NO:2), Gly-Arg-Thr-Gly (SEQ ID NO:3), Arg-Met-Ser-Leu (SEQ ID NO:4), Arg-Nle-Ser-Leu (SEQ ID NO:5), Gly-Arg-Ser-Leu (SEQ ID NO:6), Leu-Leu-Ala-Leu (SEQ ID NO:7), Leu-Gly-Ile-Ala (SEQ ID NO:8), Gln-Gly-Ile-Leu (SEQ ID NO:9), Gln-Gly-Leu-Leu (SEQ ID NO:10), Gln-Gly-Ile-Ala (SEQ ID NO:11), Gln-Ala-Ile-Ala (SEQ ID NO:12), Gln-Gly-Ile-Ala (SEQ ID NO:13), Glu-Gly-Leu-Arg (SEQ ID NO:14), Gly-His-Phe-Arg (SEQ ID NO:15), Leu-Glu-Val-Met (SEQ ID NO:16), Leu-Glu-Val-Nle (SEQ ID NO:17), Ile-His-Ile-Gln (SEQ ID NO:18), Ala-Asn-Tyr-Asn (SEQ ID NO:19), Ala-Gly-Glu-Arg (SEQ ID NO:20), Ala-Gly-Phe-Ala (SEQ ID NO:21), Gln-Gly-Leu-Ala (SEQ ID NO:22), Ala-Gln-Phe-Val (SEQ ID NO:23), Ala-Gly-Val-Glu (SEQ ID NO:24), Phe-Cys-Met-Leu (SEQ ID NO:25), Phe-Cys-Nle-Leu (SEQ ID NO:26), His-Phe-Leu-Arg (SEQ ID NO:27), Glu-Leu-Phe-Ser (SEQ ID NO:28), Leu-Ala-Phe-Leu (SEQ ID NO:29), His-Phe-Val-Arg (SEQ ID NO:30), Leu-Leu-His-Asn (SEQ ID NO:31), Gln-Tyr-Thr-Tyr (SEQ ID NO:32), Gln-Tyr-Ser-Asn (SEQ ID NO:33), or Ile-Tyr-Ser-Gln (SEQ ID NO:34).

This invention also includes compositions of formula II in which $C^1_5$ is Asp or Lys; $C^1_4$ is Ala, Met, Nle, Aib, Pro, Ile, Gly, Asp Arg, Thr, Lys, Phe, Gln, or Ser; and $C^1_3$ is Ile, Aib, Pro, Thr, Ser, Ala, Val, Gly, Phe, or Gln. Particularly preferred are compositions in which the $C^1$ conformation determining region ($C^1_5$-$C^1_4$-$C^1_3$) is Asp-Ala-Ile, Asp-Ile-Pro, Asp-Aib-Pro, Asp-Gly-Pro, Asp-Asp-Pro, Asp-Arg-Pro, Asp-Ile-Aib, Asp-Aib-Aib, Asp-Gly-Aib, Asp-Asp-Aib or Asp-Arg-Aib.

Preferred protease indicators include compositions of formula II in which $P_2'$ is a Pro, in which case $C^2$ is a single amino acid. Thus Y is formula IV in which $C^2_3$ is preferably a Cys or a Lys. In another embodiment, Y is formula III and $C^2_3$ is Pro and $C^2_4$ is Cys or a Lys. In yet another preferred embodiment, $S^1$ is Lys and/or $S_2$ is Gly-Tyr.

In a particularly preferred embodiment $F^1$ is a fluorophore having an excitation wavelength ranging from 315 nm to about 650 nm, $F^2$ is a fluorophore having an excitation wavelength ranging from 315 nm to about 650 nm or both $F^1$ and $F^2$ are fluorophores having excitation and absorbtion wavelengths ranging from 315 nm to about 650 nm. $F^1$ may be the donor fluorophore with $F^2$ the acceptor fluorophore, or conversely, $F^2$ may be the donor fluorophore with $F^1$ the acceptor fluorophore. $F^1$ may be 5- and/or 6-carboxytetramethylrhodamine or 7-hydroxy-4-methylcoumarin-3-actic acid, while $F^2$ may be rhodamine X acetamide, 5- and/or 6-carboxy-X-rhodamine, or 7-diethylamino-3-((4'-iodoacetyl)amino)phenyl)-4-methylcoumarin. The two fluorophores, $F^1$ and $F^2$, in a protease indicator can be the same or different.

In a particularly preferred embodiment, n and k are 0; $C^1$ is Asp-Ala-Ile; P is Pro-Nle-Ser-Ile (SEQ ID NO:1); $C^2$ is Pro-Cys; $F^1$ is 5- and/or 6-carboxytetramethylrhodamine; and $F^2$ is 5- and/or 6-carboxy-X-rhodamine. In another particularly preferred embodiment, n and k are 0; $C^1$ is Asp-Ala-Ile; P is Pro-Met-Ser-Ile (SEQ ID NO:1); $C^2$ is Pro-Cys; $F^1$ is 5-carboxytetramethylrhodamine; and $F^2$ is rhodamine X acetamide.

This invention also includes compositions in which $C^1$ is Asp-Ala-Ile; P is Pro-Met-Ser-Ile (SEQ ID NO:1) or Pro-Nle-Ser-Ile (SEQ ID NO:2); $C^2$ is Pro-Cys; and either n or k is 1 and either $S^1$ or $S^2$ is a spacer having the sequence Asp-Gly-Ser-Gly-Gly-Gly-Glu-Asp-Glu-Lys (SEQ ID NO:35), Lys-Glu-Asp-Gly-Gly-Asp-Lys (SEQ ID NO:36), Asp-Gly-Ser-Gly-Glu-Asp-Glu-Lys (SEQ ID NO:37), Asp-Gly-Gly-Gly-Lys-Lys (SEQ ID NO:38), or Lys-Glu-Asp-Glu-Gly-Ser-Gly-Asp-Lys (SEQ ID NO:39). In these compositions $F^1$ may be 5- and/or 6-carboxytetramethylrhodamine; and $F^2$ may be rhodamine X acetamide. These compositions may be conjugated to a solid support or to a lipid including membrane lipids or liposomes.

In another embodiment, any of the compositions described above may be used in a method for detecting protease activity in a sample. The sample may be a sample of "stock" protease, such as is used in research or industry, or it may be a biological sample. Thus, this invention provides for a method of detecting protease activity in a sample by contacting the sample with any of the compositions described above and then detecting a change in fluorescence of the fluorogenic composition where an increase in fluorescence indicates protease activity. The sample is preferably a biological sample which may include biological fluids such as sputum or blood, tissue samples such as biopsies or sections, and cell samples either as biopsies or in culture. Particularly preferred are tissue sections, cultured cells, cultured tissues, and the like.

DESCRIPTION OF THE PREFERRED EMBODIMENT

Definitions

Figure 1A:
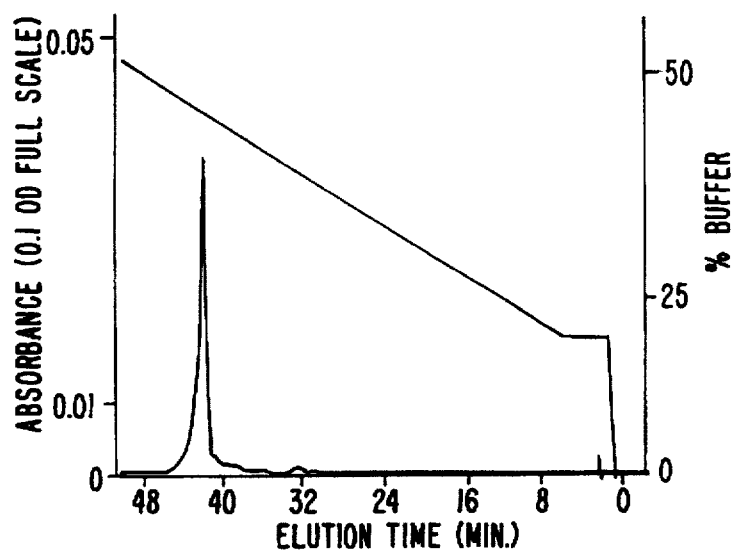
FIG. 1 shows an HPLC analysis of the D-NorFES-A protease indicator ($F^1$-Asp-Ala-Ile-Pro-Nle-Ser-Ile-Pro-Cys-$F^2$) (SEQ ID NO:40) where $F^1$ is a donor (D) fluorophore (5'-carboxytetramethylrhodamine (C2211) and $F^2$ is an acceptor (A) fluorophore (rhodamine X acetamide (R492))) before and after the addition of elastase. (A) HPLC before the addition of elastase showing the late eluting peak representing the intact indicator molecule. (B) HPLC after the addition of elastase with detection at 550 nm where both fluorophores absorb. (C) HPLC after the addition of elastase with detection at 580 nm where $F^2$ absorbs maximally.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "protease binding site" is used herein to refers to an amino acid sequence that is characteristically recognized and cleaved by a protease. The protease binding site contains a peptide bond that is hydrolyzed by the protease and the amino acid residues joined by this peptide bond are said to form the cleavage site. These amino acids are designated $P_1$ and $P_1'$ for the residues on the amino and carboxyl sides of the hydrolyzed bond respectively.

A fluorophore is a molecule that absorbs light at a characteristic wavelength and then re-emits the light most typically at a characteristic different wavelength. Fluorophores are well known to those of skill in the art and include, but are not limited to rhodamine and rhodamine derivatives, fluorescein and fluorescein derivatives, coumarins and chelators with the lanthanide ion series. A fluorophore is distinguished from a chromophore which absorbs, but does not characteristically re-emit light.

"Peptides" and "polypeptides" are chains of amino acids whose α carbons are linked through peptide bonds formed by a condensation reaction between the α carbon carboxyl group of one amino acid and the amino group of another amino acid. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include peptide mimetics such as amino acids joined by an ether as opposed to an amide bond.

The polypeptides described herein are written with the amino terminus at the left and the carboxyl terminus at the right. The amino acids comprising the peptide components of this invention are numbered with respect to the protease cleavage site, with numbers increasing consecutively with distance in both the carboxyl and amino direction from the cleavage site. Residues on the carboxyl site are either norated with a "'" as in $P_1'$, or with a letter and superscript indicating the region in which they are located. The "'" indicates that residues are located on the carboxyl side of the cleavage site.

The term "residue" or "amino acid" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "domain" or "region" refers to a characteristic region of a polypeptide. The domain may be characterized by a particular structural feature such as a β turn, an alpha helix, or a β pleated sheet, by characteristic constituent amino acids (e.g. predominantly hydrophobic or hydrophilic amino acids, or repeating amino acid sequences), or by its localization in a particular region of the folded three dimensional polypeptide. As used herein, a region or domain is composed of a series of contiguous amino acids.

The terms "protease activity" or "activity of a protease" refer to the cleavage of a peptide by a protease. Protease activity comprises the "digestion" of one or more peptides into a larger number of smaller peptide fragments. Protease activity of particular proteases may result in hydrolysis at particular peptide binding sites characteristically recognized by a particular protease. The particular protease may be characterized by the production of peptide fragments bearing particular terminal amino acid residues.

The amino acids referred to herein are described by shorthand designations as follows:

TABLE 1

Amino acid nomenclature.

| Name | Abbreviation | |
|---|---|---|
| | 3 Letter | 1 Letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| α-aminoisubutyric acid | Aib | — |

Fluorogenic Indicators of Protease Activity

This invention provides for novel fluorogenic molecules useful for detecting protease activity in a sample. The fluorogenic protease indicators of the present invention generally comprise a fluorophore (donor) linked to an "acceptor" molecule by a peptide having an amino acid sequence that is recognized and cleaved by a particular protease. The donor fluorophore typically is excited by incident radiation at a particular wavelength which it then re-emits at a different (longer) wavelength. When the donor fluorophore is held in close proximity to the acceptor molecule, the acceptor absorbs the light re-emitted by the fluorophore thereby quenching the fluorescence signal of the donor molecule. The quench occurs whether the two fluorophores are different or the same species. Thus, in addition to peptides double labeled with two different fluorophores as shown in Example 1, peptides double labeled with the same fluorophore may also be used as protease indicators (see, e.g., Example 6). Cleavage of a well-designed (i.e. a peptide of this invention) joining the donor fluorophore and the acceptor results in separation of the two molecules, release of the quenching effect and increase in florescence.

In one basic application, the fluorogenic molecules of this invention may be used to assay the activity of purified protease made up as a reagent (e.g. in a buffer solution) for experimental or industrial use. Like many other enzymes, proteases may loose activity over time, especially when they are stored as their active forms. In addition, many proteases exist naturally in an inactive precursor form (e.g. a zymogen) which itself must be activated by hydrolysis of a particular peptide bond to produce the active form of the enzyme prior to use. Because the degree of activation is variable and because proteases may loose activity over time, it is often desirable to verify that the protease is active and to often quantify the activity before using a particular protease in a particular application.

Previous approaches to verifying or quantifying protease activity involve combining an aliquot of the protease with its substrate, allowing a period of time for digestion to occur and then measuring the amount of digested protein, most typically by HPLC. This approach is time consuming, utilizes expensive reagents, requires a number of steps and entails a considerable amount of labor. In contrast, the fluorogenic reagents of the present invention allow rapid determination of protease activity in a matter of minutes in a single-step procedure. An aliquot of the protease to be tested is simply added to, or contacted with, the fluorogenic reagents of this invention and the subsequent change in fluorescence is monitored (e.g., using a fluorimeter).

In addition to determining protease activity in "reagent" solutions, the fluorogenic compositions of the present invention may be utilized to detect protease activity in biological samples. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Previously described fluorogenic protease indicators typically absorb light in the ultraviolet range (e.g., Wang et al., supra.). They are thus unsuitable for sensitive detection of protease activity in biological samples which typically contain constituents (e.g., proteins) that absorb in the ultraviolet range. In contrast, the fluorescent indicators of the present invention both absorb and emit in the visible range (400 nm to about 700 nm). These signals are therefore not readily quenched by, nor is activation of the fluorophores, that is, absorption of light, interfered with by background molecules; therefore they are easily detected in biological samples.

In addition, unlike previous fluorogenic protease indicators which often utilize a fluorophore and a quenching chromophore, the indicators of the present invention may utilize two fluorophores (i.e., fluorophore as both donor and acceptor) or the same two fluorophores effectively forming a ground-state dimer when joined by the one of the peptide backbones of this invention. Pairs of fluorophores may be selected that show a much higher degree of quenching than previously described chromophore/fluorophore combinations. In fact, previous compositions have been limited to relatively low efficiency fluorophores because of the small degree of quenching obtainable with the matching chromophore (Wang et al. supra.). In contrast, the fluorogenic protease indicators of this invention utilize high efficiency fluorophores and are able to achieve a high degree of quenching while providing a strong signal when the quench is released by cleavage of the peptide substrate. The high signal allows detection of very low levels of protease activity. Thus the fluorogenic protease indicators of this invention are particularly well suited for in situ detection of protease activity.

The fluorogenic protease indicators of the present have the general formula:

$$F^1-C^1-P-C^2-F^2 \quad \text{I}$$
$$\quad\ \ |\quad\quad\ \ |$$
$$\ \ (S^1)_m\quad (S^2)_k$$

where P is a peptide comprising a protease binding site, $F^1$ and $F^2$ are fluorophores, $C^1$ and $C^2$ are conformation determining regions, and $S^1$ and $S^2$ are optional peptide spacers. $F^1$ may be the donor fluorophore while $F^2$ is the acceptor fluorophore, or conversely, $F^2$ may be the donor fluorophore while $F^1$ is the acceptor fluorophore, or $F^1$ and $F^2$ may be identical. The protease binding site provides an amino acid sequence (a peptide) that is recognized and cleaved by the protease whose activity the indicator is designed to reveal. The protease binding site is typically a peptide ranging in length from about 2 to about 8, more preferably from about 2 to about 6 and most preferably 2 to about 4 amino acids in length.

The conformation determining region is an amino acid sequence that introduces a bend into the molecule. The combined effect of the two conformation determining regions is to put two bends into the peptide backbone of the composition so that it achieves a substantially U-shaped conformation. This U-shaped conformation brings the fluorophores attached to the amino and carboxyl termini of $C^1$ and $C^2$ respectively into closer proximity to each other. The fluorophores are thus preferably positioned adjacent to each other at a distance less than about 100 angstroms. The fluorophores ($F^1$ and $F^2$) are typically conjugated directly to the conformation determining regions, although they may be joined by linkers. The optional spacers ($S^1$ and $S^2$) when present, are used to link the composition to a solid support or to anchor the composition to a component of a biological sample (e.g., to a cellular membrane).

The substantially U-shaped conformation increases the protease specificity of the composition. The amino acid sequences comprising the conformation determining regions (the arms of the U) are less accessible to the enzyme due to steric hinderance with each other and with the attached fluorophores. The protease binding site (presented on the bottom portion of the U) is relatively unobstructed by either the fluorophore or the conformational determining region and is thus readily accessible to the protease.

Protease Binding Site and Conformation Determining Regions

The protease binding site and conformation determining regions form a contiguous amino acid sequence (peptide). The protease binding site is an amino acid sequence that is recognized and cleaved by a particular protease. It is well known that various proteases cleave peptide bonds adjacent to particular amino acids. Thus, for example, trypsin cleaves peptide bonds following basic amino acids such as arginine and lysine and chymotrypsin cleaves peptide bonds following large hydrophobic amino acid residues such as tryptophan, phenylalanine, tyrosine and leucine. The serine protease elastase cleaves peptide bonds following small hydrophobic residues such as alanine.

A particular protease, however, will not cleave every bond in a protein that has the correct adjacent amino acid. Rather, the proteases are specific to particular amino acid sequences which serve as recognition domains for each particular protease.

Any amino acid sequence that comprises a recognition domain and can thus be recognized and cleaved by a protease is suitable for the "protease binding site" of the fluorogenic protease indicator compositions of this invention. Known protease substrate sequences and peptide inhibitors of proteases posses amino acid sequences that are recognized by the specific protease they are cleaved by or that they inhibit. Thus known substrate and inhibitor sequences provide the basic sequences suitable for use in the protease recognition region. A number of protease substrates and inhibitor sequences suitable for use as protease binding domains in the compositions of this invention are indicated in Table 2. One of skill will appreciate that this is not a complete list and that other protease substrates or inhibitor sequences may be used.

The amino acid residues comprising the protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

$$P_2\text{-}P_1\text{-}P_1'\text{-}P_2'$$

and the protease would cleave the binding region between $P_1$ and $P_1'$.

In a preferred embodiment, the protease binding region of the fluorogenic protease indicators of the present invention is selected to be symmetric about the cleavage site. Thus, for example, where a binding region is Ile-Pro-Met-Ser-ILe (SEQ ID NO:41)

(e.g. α-1 anti-trypsin) and the cleavage occurs between Met and Ser then a 4 amino acid residue binding region based on this sequence would be:

$P_2$ $P_1$ $P_1'$ $P_2'$-Pro-Met-Ser-ILe-(SEQ ID NO:1)

Other examples of binding domains selected out of longer sequences are provided in Table 2. The remaining amino or carboxyl residues that are not within the protease binding domain may remain as part of the conformation determining regions subject to certain limitations as will be explained below. Thus, in the instant example, the amino terminal Ile may be incorporated into the $C^1$ conformation determining region.

Various amino acid substitutions may be made to the amino acids comprising the protease binding domain to increase binding specificity, to eliminate reactive side chains, or to reduce the conformational entropy (decrease degrees of freedom) of the molecule. Thus, for example, it is often desirable to substitute methionine (Met) residues, which bear a oxidizable sulfur, with norleucine. Thus, in the example given, a preferred protease binding region will have the sequence:

$P_2$ $P_1$ $P_1'$ $P_2'$-Pro-Nle-Ser-ILe-(SEQ ID NO:2)

Conformation Determining Regions

Conformation determining regions ($C^1$ and $C^2$) are peptide regions on either end of the protease cleavage region that both stiffen and introduce bends into the peptide backbone of the fluorogenic protease indicator molecules of this invention. The combination of the two conformation determining regions and the relatively straight protease cleavage region produces a roughly U-shaped molecule with the cleavage site at the base (middle) of the "U". The term U-shaped is, of course, approximate, the point being that, as described below, the fluorophores are held relatively rigidly in close juxtaposition (e.g., less than about 100 angstroms).

Amino acids such as proline (Pro) and α-aminobutyric acid (Aib) are selected both to introduce bends into the peptide molecule and to increase the rigidity of the peptide backbone. The $C^1$ and $C^2$ domains are selected such that the "arms" of the U are rigid and the attached fluorophores are localized adjacent to each other at a separation of less than about 100 angstroms. In order to maintain the requisite stiffness of the peptide backbone and placement of the fluorophores, the conformation determining regions are preferably 4 amino acids in length or less, or alternatively are greater than about 18 amino acids in length and form a stable alpha helix conformation or a β-pleated sheet.

In a preferred embodiment, the peptide backbone of the fluorogenic protease indicators of the present invention will comprise a tripeptide $C^1$ region, a tetrapeptide P region and a single amino acid or dipeptide $C^2$ region. These compounds may be represented by the formula:

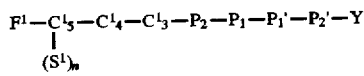   II where Y is either

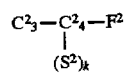   III or

   IV

In these formulas the peptide binding region is designated $-P_2-P_1-P_1'-P_2'-$, while the amino acid residues of conformation determining regions $C^1$ and $C^2$ are designated $-C^1_5-C^1_4-C^1_3-$ and $-C^2_3-C^2_4-$ respectively. The $C^2$ region may either be an amino acid or a dipeptide. Whether the $C^2$ region is a dipeptide or an amino acid, the $F^2$ fluorophore and the $S^2$ spacer, when present, are always coupled to the carboxyl terminal residue of $C^2$. When a spacer is present on the $C^2$ region, it is attached the carboxyl terminal residue of $C^2$ by a peptide bond to the α carboxyl group.

As indicated above, the conformation determining regions typically contain amino acid residues such as a proline (Pro) that introduce a bend into the molecule and increase its stiffness. One of skill in the art will appreciate, however that where the terminal residues of the protease binding region (P) are themselves bend-creating residues such as proline, it is not necessary to locate a bend-creating residue at the position closest to P in the C region attached to that terminus. The conformation determining regions are thus designed by first determining the protease binding region, as described above, determining the "left-over" residues that would lie in the conformation determining regions, and if necessary, modifying those residues according to the following guidelines:

1. If the $P_2'$ site is not a Pro then $C^2$ is a dipeptide (Formula III) Pro-Cys, Aib-Cys, Pro-Lys, or Aib-Lys, while conversely, if the $P_2'$ site is a Pro then $C^2$ is a single amino acid residue (Formula IV) Cys or Lys.

2. If the $P_2$ site is not a Pro then $C^1$ is a tripeptide consisting of Asp-$C^1_4$-Pro, Asp-$C^1_4$-Aib, Asp-Aib-Pro, Asp-Pro-$C^1_3$, Asp-Aib-$C^1_3$, Asp-Pro-Aib, or Asp-Aib-Aib, while if the $P_2$ site is a Pro residue then group $C^1$ is a tripeptide consisting of Asp-$C^1_4$-$C^1_3$ or Asp-$C^1_4$-Aib.

3. If the $P_3$ ($C^1_3$) residue is a Pro then $C^1$ is a tripepride consisting of Asp-$C^1_4$-Pro or Asp-Aib-Pro.

4. If the $P_4$ ($C^1_4$) residue is a Pro then $C^1$ is a tripepride consisting of Asp-Pro-$C^1_3$ or Asp-Pro-Aib.

5. If $P_2$ and $C^1_3$ are both not prolines then $C^1$ is a tripepride consisting of Asp-Pro-$C^1_3$, Asp-Aib-$C^1_3$, AsP-$C^1_4$-Pro, AsP-$C^1_4$-Aib, Asp-Pro-Aib, or Asp-Aib-Pro.

As indicated above, any methionine (Met) may be replaced with a norleucine (Nle). A number of suitable peptide backbones consisting of $C^1$, P and $C^2$ are provided in Table 2.

TABLE 2

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/Inhibitor | CDR ($C^1$) | | | Protease Binding Site (P) | | | | CDR ($C^2$) | |
|---|---|---|---|---|---|---|---|---|---|
| | $C_5^1$ | $C_4^1$ | $C_3^1$ | $P_2$ | $P_1$ | $P_1'$ | $P_2'$ | $C_3^2$ | $C_4^2$ |
| α-1 anti-trypsin | Asp | Ala | Ile | Pro | Met Nle | Ser | Ile | Pro Aib | Cys Lys |
| plasminogen activator inhibitor 2 | Asp | Met Aib Pro | Thr Aib Pro | Gly | Arg | Thr | Gly | Pro Aib | Cys Lys |
| neutrophil leukocyte elastase inhibitor | Asp | Ala Aib | Thr Aib Pro | Phe | Cys | Met Nle | Leu | Pro Aib | Cys Lys |
| anti-plasmin inhibitor | Asp | Aib | Ser Aib Pro | Arg | Met Nle | Ser | Leu | Pro Aib | Cys Lys |
| anti α-1 thrombin | Asp | Ile Aib | Ala Aib Pro | Gly | Arg | Ser | Leu | Pro Aib | Cys Lys |
| α-1 antichymotrypsin | Asp | Aib | Thr Aib Pro | Leu | Leu | Ser | Leu | Pro Aib | Cys Lys |
| interstitial type III (human liver) collagen | Asp | Gly Aib | Pro Aib | Leu | Gly | Ile | Ala | Pro Aib | Cys Lys |

TABLE 2-continued

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/Inhibitor | CDR ($C^1$) | | | Protease Binding Site (P) | | | | CDR ($C^2$) | |
|---|---|---|---|---|---|---|---|---|---|
| | $C_5^1$ | $C_4^1$ | $C_3^1$ | $P_2$ | $P_1$ | $P_1'$ | $P_2'$ | $C_3^2$ | $C_4^2$ |
| type I collagen for collagenase Bovine α 1 | Asp | Gly Aib Pro | Pro Aib | Gln | Gly | Ile | Leu | Pro Aib | Cys Lys |
| type I collagen chick α2 | Asp | Gly Aib Pro | Pro Aib | Gln | Gly | Leu | Leu | Pro Aib | Cys Lys |
| human α1 type II collagen | Asp | Gly Aib Pro | Pro Aib | Gln | Gly | Ile | Ala | Pro Aib | Cys Lys |
| type III collagen - AIA | Asp | Gly Aib Pro | Pro Aib | Gln | Ala | Ile | Ala | Pro Aib | Cys Lys |
| type III collagen (human skin) | Asp | Gly Aib Pro | Pro Aib | Gln | Gly | Ile | Ala | Pro Aib | Cys Lys |
| human α 2 macroglobulin | Asp | Gly Aib Pro | Pro Aib | Glu | Gly | Leu | Arg | Pro Aib | Cys Lys |
| stromelysin cleavage sites of stromelysin-1d | Asp | Asp Aib Pro | Val Aib Pro | Gly | His | Phe | Arg | Pro Aib | Cys Lys |
| stromelysin cleavage sites of stromelysin-1 | Asp | Asp Aib Pro | Thr Aib Pro | Leu | Glu | Val | Met Nle | Pro Aib | Cys Lys |
| stromelysin cleavage site of proteoglycan link protein | Asp | Arg Aib Pro | Ala Aib Pro | Ile | His | Ile | Gln | Pro Aib | Cys Lys |
| gelatinase type IV collagenase site of 72 K gelatinases | Asp | Asp Aib Pro | Val Aib Pro | Ala | Asn | Tyr | Asn | Pro Aib | Cys Lys |
| gelatinase type IV cleavage of gelatin | Asp | Gly Aib Pro | Pro Aib | Ala | Gly | Glu | Arg | Pro Aib | Cys Lys |
| gelatinase type IV cleavage of gelatin | Asp | Gly Aib Pro | Pro Aib | Ala | Gly | Phe | Ala | Pro Aib | Cys Lys |
| type III collagen (human skin) | Asp | Gly Aib Pro | Pro Aib | Gln | Gly | Leu | Ala | Pro Aib | Cys Lys |
| Human FIB-CL propeptide | Asp | Asp Aib Pro | Val Aib Pro | Ala | Gln | Phe | Val | Pro Aib | Cys Lys |
| Cathepsin D (Thyroglobulin Fragment Tg1) | Asp | Asp Aib Pro | Gly Pro Aib | His | Phe | Leu | Arg | Pro Aib | Cys Lys |
| Cathepsin D (Thyroglobulin Fragment Tg2) | Asp | Thr Aib Pro | Thr Pro Aib | Glu | Leu | Phe | Ser | Pro Aib | Cys Lys |
| Cathepsin D (Thyroglobulin Fragment Tg3) | Asp | Lys Aib Pro | Phe Pro Aib | leu | Ala | Phe | Leu | Pro Aib | Cys Lys |
| Cathepsin D (Thyroglobulin Fragment Tg4) | Asp | Phe Aib Pro | Ser Pro Aib | His | Phe | Val | Arg | Pro Aib | Cys Lys |
| Prostate Specific Antigen (PSA) (Seminolgelin, Sg) Sg1 | Asp | Gln Aib Pro | Gln Pro Aib | Leu | Leu | His | Asn | Pro Aib | Cys Lys |
| Prostate Specific Antigen (PSA) (Seminolgelin, Sg) Sg2 | Asp | Ser Aib Pro | Ile Pro Aib | Gln | Tyr | Thr | Tyr | Pro Aib | Cys Lys |
| Prostate Specific Antigen (PSA) (Seminolgelin, Sg) Sg3 | Asp | Ser Aib Pro | Ser Pro Aib | Gln | Tyr | Ser | Asn | Pro Aib | Cys Lys |

TABLE 2-continued

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/Inhibitor | CDR ($C^1$) | | | Protease Binding Site (P) | | | | CDR ($C^2$) | |
|---|---|---|---|---|---|---|---|---|---|
| | $C_5^1$ | $C_4^1$ | $C_3^1$ | $P_2$ | $P_1$ | $P_1'$ | $P_2'$ | $C_3^2$ | $C_4^2$ |
| Prostate Specific Antigen (PSA) (Seminolgelin, Sg) Sg4 | Asp | Ser *Aib Pro* | Ser *Pro Aib* | Ile | Tyr | Ser | Gln | Pro *Aib* | Cys Lys |
| Gelatin α1 (type 1) | Asp | Gly *Aib Pro* | Pro *Aib* | Ala | Gly | Val | Gln | Pro *Aib* | Cys Lys |

[1] In a preferred embodiment, the sequence may be followed by an $S_2$ spacer of Gly—Tyr. Thus, for example, where $C_4^2$ is Lys, $C_4^2$—$S_2$ is Lys—Gly—Tyr.

"Donor" an "Acceptor" Fluorophores

A fluorophore excited by incident radiation absorbs light and then subsequently re-emits that light at a different (longer) wavelength. However, in the presence of a second class of molecules, known as "acceptors" the light emitted by a so-called donor fluorophore is absorbed by the acceptor thereby quenching the fluorescence signal of the donor. Thus, use of two fluorophores, as opposed to a fluorophore/chomophore pair, allows a clearer assessment of the overlap between the emission spectrum of the donor and the excitation spectrum of the acceptor. This facilitates the design of a peptide backbone that allows allowing optimization of the quenching. This results in a high efficiency donor/acceptor pair facilitating the detection of low concentrations of protease activity. Thus, although a fluorophore/chromophore combination may be suitable, in a preferred embodiment, the fluorogenic protease inhibitors of this invention will comprise two fluorophores.

The "donor" and "acceptor" molecules are typically selected as a matched pair such that the absorption spectra of the acceptor molecule overlaps the emission spectrum of the donor molecule as much as possible. In addition, the donor and acceptor fluorophores are preferably selected such that both the absorption and the emission spectrum of the donor molecule is in the visible range (400 nm to about 700 nm). The fluorophores thereby provide a signal that is detectable in a biological sample thus facilitating the detection of protease activity in biological fluids, tissue homogenates, in situ in tissue sections, and the like. The emission spectra, absorption spectra and chemical composition of many fluorophores are well known to those of skill in the art (see, for example, *Handbook of Fluorescent Probes and Research Chemicals*, R. P. Haugland, ed. which is incorporated herein by reference).

Preferred fluorophore pairs include the rhodamine derivatives. Thus, for example 5-carboxytetramethylrhodamine or the succinimidyl ester of 5- and/or 6-carboxytetramethylrhodamine (C211 and C1171, respectively, available from Molecular Probes, Eugene, Oreg. U.S.A.) (Formula V) is a particularly preferred donor molecule

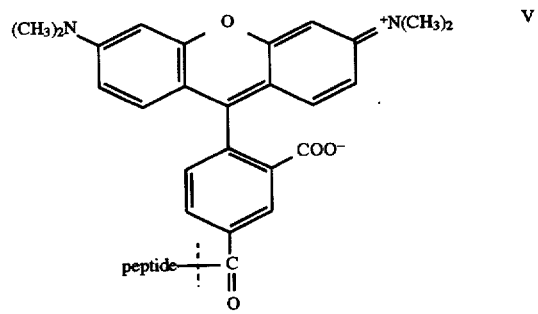

and rhodamine X acetamide (R492 from Molecular Probes) (Formula VI) or the succinimidyl ester of 5- and/or 6-carboxy-X-rhodamine (C1309 from Molecular Probes) is a particularly preferred receptor molecule. These fluorophores are particularly

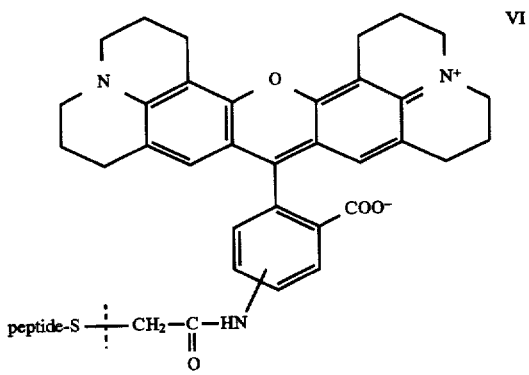

preferred since the excitation and emission of both members of this donor/acceptor pair are in the visible wavelengths, the molecules have high extinction coefficients and the molecules have high fluorescence yields in solution. The extinction coefficient is a measure of the light absorbance at a particular wavelength by the chromophore and is therefore related to its ability to quench a signal, while the fluorescence yield is the ratio of light absorbed to light re-emitted and is a measure of the efficiency of the fluorophore and thus effects the sensitivity of the protease indicator.

Of course, while not most preferred, fluorophores that absorb and emit in the ultraviolet may also be used in the protease indicators of the present invention. One particularly preferred ultraviolet absorbing pair of fluorophores is 7-hydroxy-4-methylcoumarin-3-acetic acid as the donor molecule (Formula VII)

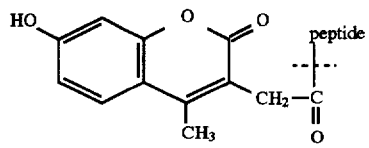

and 7-diethylamino-3-((4'-iodoacetyl)amino)phenyl)-4-methylcoumarin (Formula VIII) as the acceptor molecule.

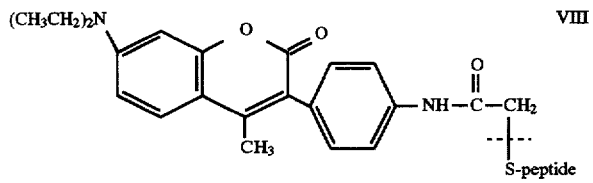

These and other fluorophores are commercially available from a large number of manufacturers such as Molecular Probes (Eugene, Oreg., U.S.A.).

It was a surprising discovery that fluorophores having matched absorption and emission spectra are not required in the practice of the present invention. In fact, a single species of fluorophore, when joined to the polypeptide backbones of this invention in the positions occupied by $F^1$ and $F^2$, is capable of quenching itself. Moreover, this quenching is fully released when the peptide backbone is cleaved.

Without being bound to a particular theory, it is believed that quenching is accomplished by the formation of ground state dimers wherein the electron orbitals of the two fluorophores interact resulting in reciprocal quenching. It is the limited conformational entropy of the peptide backbones of this invention that forces fluorophores into close enough proximity to effectively form a ground state dimer.

Thus, in a preferred embodiment, the protease indicators of this invention include only a single species of fluorophore. In this embodiment, there is no need to match emission or absorption spectra since only a single fluorophore is used. Thus a wide variety of fluorophores can be used effectively. In addition, the use of a single fluorophore greatly simplifies synthesis chemistry.

Preparation of Fluorogenic Indicators

The fluorogenic protease indicators of the present invention are preferably prepared by first synthesizing the peptide backbone, i.e. the protease cleavage site (P), the two conformation determining regions ($C^1$ and $C^2$), and the spacers ($S^1$ and $S^2$) if present. The fluorophores are then chemically conjugated to the peptide. The fluorophores are preferably conjugated directly to the peptide however, they may also be coupled to the peptide through a linker. Finally, where the fluorogenic protease indicator is to be bound to a solid support, it is then chemically conjugated to the solid support via the spacer ($S^1$ or $S^2$) either directly or through a linker.

a) Preparation of the peptide backbone

Solid phase peptide synthesis in which the C-terminal amino acid of the sequence is attached to an insoluble support followed by sequential addition of the remaining amino acids in the sequence is the preferred method for preparing the peptide backbone of the compounds of the present invention. Techniques for solid phase synthesis are described by Barany and Merrifield, Solid-Phase Peptide Synthesis; pp. 3–284 in The Peptides: Analysis, Synthesis, Biology. Vol. 2: Special Methods in Peptide Synthesis, Part A., Merrifield, et al. J. Am. Chem. Soc. 85, 2149–2156 (1963), and Gross and Meienhofer, eds. Academic press, New York, 1980 and Stewart et al., Solid Phase Peptide Synthesis, 2nd ed. Pierce Chem. Co., Rockford, Ill. (1984) which are incorporated herein by reference. Solid phase synthesis is most easily accomplished with commercially available peptide synthesizers utilizing FMOC or TBOC chemistry. The chemical synthesis of the peptide component of a fluorogenic protease indicator is described in detail in Examples 1 and 2.

In a particularly prefered embodiment, peptide synthesis is performed using Fmoc synthesis chemistry. The side chains of Asp, Ser, Thr and Tyr are preferably protected using S-trityl and S-t-butylthio, and Lys residues are preferably protected using t-Boc, Fmoc and 4-methyltrityl for lysine residues. Appropriately protected amino acid reagents are commercially available. The use of multiple protecting groups allows selective deblocking and coupling of a fluorophore to any particular desired side chain. Thus, for example, t-Boc deprotection is accomplished using TFA in dichloromethane, Fmoc deprotection is accomplished using 20% (v/v) piperidine in DMF or N-methylpyrolidone, and 4-methyltrityl deprotection is accomplished using 1 to 5 % (v/v) TFA in water or 1% TFA and 5% triisopropylsilane in DCM, S-t-butylthio deprotection is accomplished in aqueous mercaptoethanol (10%), t-butyl and t-boc and S-trityl deprotection is accomplished using TFA:phenol:water:thioanisol:ethanedithiol (85:5:5:2.5:2.5), and t-butyl and t-Boc deprotection is accomplished using TFA: phenol:water (95:5:5). Detailed synthesis, deprotection and fluorophore coupling protocols are provided in Examples 1 and 2.

Alternatively, the peptide components of the fluorogenic protease indicators of the present invention may be synthesized utilizing recombinant DNA technology. Briefly, a DNA molecule encoding the desired amino acid sequence is synthesized chemically by a variety of methods known to those of skill in the art including the solid phase phosphoramidite method described by Beaucage and Carruthers, Tetra. Letts. 22: 1859–1862 (1981), the triester method according to Matteucci, et al., J. Am. Chem. Soc., 103:3185 (1981), both incorporated herein by reference, or by other methods known to those of skill in the art. It is preferred that the DNA be synthesized using standard β-cyanoethyl phosphoramidites on a commercially available DNA synthesizer using standard protocols.

The oligonucleotides may be purified, if necessary, by techniques well known to those of skill in the art. Typical purification methods include, but are not limited to gel electrophoresis, union exchange chromatography (e.g. Mono-Q column, Pharmacia-LKB, Piscataway, N.J., U.S.A.), or reverse phase high performance liquid chromatography (HPLC). Method of protein and peptide purification are well known to those of skill in the art. For a review of standard techniques see, Methods in Enzymology Volume 182: Guide to Protein Purification, M. Deutscher, ed. (1990), pages 619–626, which are incorporated herein by reference.

The oligonucleotides may be converted into double stranded DNA either by annealing with a complementary oligonucleotide or by polymerization with a DNA polymerase. The DNA may then be inserted into a vector under the control of a promoter and used to transform a host cell so that the cell expresses the encoded peptide sequence. Methods of cloning and expression of peptides are well known to those of skill in the art. See, for example, Sambrook, et al., Molecular Cloning: A Laboratory Manual (2nd Ed., Vols. 1–3, Cold Spring Harbor Laboratory (1989)), Methods in Enzymology, Vol. 152: Guide to Molecular Cloning Techniques (Berger and Kimmel (eds.), San Diego: Academic Press, Inc. (1987)), or Current Protocols in

*Molecular Biology*, (Ausubel, et al. (eds.), Greene Publishing and Wiley-Interscience, New York (1987), which are incorporated herein by reference.

b) Linkage of the florophores to the peptide backbone

The fluorophores are linked to the peptide backbone by any of a number of means well known to those of skill in the art. In a preferred embodiment, the fluorophore is linked directly from a reactive site on the fluorophore to a reactive group on the peptide such as a terminal amino or carboxyl group, or to a reactive group on an amino acid side chain such as a sulfur, an amino, a hydroxyl, or a carboxyl moiety. Many fluorophores normally contain suitable reactive sites. Alternatively, the fluorophores may be derivatized to provide reactive sites for linkage to another molecule. Fluorophores derivatized with functional groups for coupling to a second molecule are commercially available from a variety of manufacturers. The derivatization may be by a simple substitution of a group on the fluorophore itself, or may be by conjugation to a linker. Various linkers are well known to those of skill in the art and are discussed below.

As indicated above, in a preferred embodiment, the fluorophores are directly linked to the peptide backbone of the protease indicator. Thus, for example, the 5'-carboxytetramethylrhodamine (C2211) fluorophore may be linked to aspartic acid via the alpha amino group of the amino acid as shown in Formula V. The iodoacetamide group of rhodamine X acetamide (R492)) may be linked by reaction with the sulfhydryl group of a cysteine as indicated in formula VI. Means of performing such couplings are well known to those of skill in the art, and the details of one such coupling are provided in Example 1.

One of skill in the art will appreciate that when the peptide spacers ($S^1$ or $S^2$) are present (as is discussed below), the fluorophores are preferably linked to the conformation determining regions through a reactive group on the side chain of the terminal amino acid of $C^1$ or $C^2$ as the spacers themselves form a peptide linkage with the terminal amino and carboxyl groups of $C^1$ or $C^2$ respectively.

c) Selection of spacer peptides and linkage to a solid support

The fluorogenic protease indicators of the present invention may be obtained in solution or linked to a solid support. A "solid support" refers to any solid material that does not dissolve in or react with any of the components present in the solutions utilized for assaying for protease activity using the fluorogenic protease indicator molecules of the present invention and that provides a functional group for attachment of the fluorogenic molecule. Solid support materials are well known to those of skill in the art and include, but are not limited to silica, controlled pore glass (CPG), polystyrene, polystyrene/latex, carboxyl modified teflon, dextran, derivatized polysaccharides such as agar beating amino, carboxyl or sulfhydryl groups, various plastics such as polyethylene, acrylic, and the like. Also of use are "semi-solid" supports such as lipid membranes as found in cells and in liposomes. One of skill will appreciate that the solid supports may be derivatized with functional groups (e.g. hydroxyls, mines, carboxyls, esters, and sulfhydryls) to provide reactive sites for the attachment of linkers or the direct attachment of the peptide.

The fluorogenic protease indicators may be linked to a solid support directly through the fluorophores or through the peptide backbone comprising the indicator. Linkage through the peptide backbone is most preferred.

When it is desired to link the indicator to a solid support through the peptide backbone, the peptide backbone may comprise an additional peptide spacer (designated $S^1$ or $S^2$ in Formula I). The spacer may be present at either the amino or carboxyl terminus of the peptide backbone and may vary from about 1 to about 50 amino acids, more preferably from 1 to about 20 and most preferably from 1 to about 10 amino acids in length. Particularly preferred spacers include Asp-Gly-Ser-Gly-Gly-Gly-Glu-Asp-Glu-Lys (SEQ ID No:35), Lys-Glu-Asp-Gly-Gly-Asp-Lys (SEQ ID NO:36), Asp-Gly-Ser-Gly-Glu-Asp-Glu-Lys (SEQ ID NO:37), and Lys-Glu-Asp-Glu-Gly-Ser-Gly-Asp-Lys (SEQ ID NO:39).

The amino acid composition of the peptide spacer is not critical as the spacer just serves to separate the active components of the molecule from the substrate thereby preventing undesired interactions. However, the amino acid composition of the spacer may be selected to provide amino acids (e.g. a cysteine or a lysine) having side chains to which a linker or the solid support itself, is easily coupled. Alternatively the linker or the solid support itself may be attached to the amino terminus of $S^1$ or the carboxyl terminus of $S^2$.

In a preferred embodiment, the peptide spacer is actually joined to the solid support by a linker. The term "linker", as used herein, refers to a molecule that may be used to link a peptide to another molecule, (e.g. a solid support, fluorophore, etc.). A linker is a hetero or homobifunctional molecule that provides a first reactive site capable of forming a covalent linkage with the peptide and a second reactive site capable of forming a covalent linkage with a reactive group on the solid support. The covalent linkage with the peptide (spacer) may be via either the terminal carboxyl or amino groups or with reactive groups on the amino acid side-chain (e.g. through a disulfide linkage to a cysteine).

Suitable linkers are well known to those of skill in the art and include, but are not limited to, straight or branched-chain carbon linkers, heterocyclic carbon linkers, or peptide linkers. As indicated above, the linkers may be joined to the carboxyl and amino terminal amino acids through their terminal carboxyl or amino groups or through their reactive side-chain groups.

Particularly preferred linkers are capable of forming covalent bonds to amino groups, carboxyl groups, or sulfhydryl. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Finally, sulfhydryl-binding linkers include reactive groups such as sulfhydryl groups, acrylates, isothiocyanates, isocyanates and the like. Particularly preferred linkers include sulfoMBS (m-maleimidobenzoyl-N-hydroxysulfosuccinimide ester) for linking amino groups (e.g. an amino group found on a lysine residue in the peptide) with sulfhydryl groups found on the solid support, or vice versa, for linking sulfhydryl groups (e.g. found on a cysteine residue of the peptide) with amino groups found on the solid support. Other particularly preferred linkers include EDC (1-ethyl-3-(3-dimethylaminopropryl)-carbodiimide) and bis-(sulfosuccinimidyl substrate). Other suitable linkers are well known to those of skill in the art.

The fluorogenic compounds of the present invention may be linked to the solid support through either the $S^1$ or the $S^2$ spacer such that the donor fluorophore is either retained on the solid support after cleavage of the molecule by a protease or such that the donor fluorophore goes into solution after cleavage. In the former case, the substrate is then assayed for fluorescence to detect protease activity, while in the later case the solution is assayed for fluorescence to detect protease activity.

Detection of Protease Activity

The present invention also provides methods for utilizing the fluorogenic protease indicators to detect protease activity in a variety of contexts. Thus, in one embodiment, the present invention provides for a method of using the fluorogenic indicators to verify or quantify the protease activity of a stock solution of a protease used for experimental or industrial purposes. Verification of protease activity of stock protease solutions before use is generally recommended as proteases often to loose activity over time (e.g. through self-hydrolysis) or to show varying degrees of activation when activated from zymogen precursors.

Assaying for protease activity of a stock solution simply requires adding a quantity of the stock solution to a fluorogenic protease indicator of the present invention and measuring the subsequent increase in fluorescence. The stock solution and the fluorogenic indicator may also be combined and assayed in a "digestion buffer" that optimizes activity of the protease. Buffers suitable for assaying protease activity are well known to those of skill in the art. In general, a buffer will be selected whose pH corresponds to the pH optimum of the particular protease. For example, a buffer particularly suitable for assaying elastase activity consists of 50 mM sodium phosphate, 1 mM EDTA at pH 8.9. The measurement is most easily made in a fluorometer, and instrument that provides an "excitation" light source for the fluorophore and then measures the light subsequently emitted at a particular wavelength. Comparison with a control indicator solution lacking the protease provides a measure of the protease activity. The activity level may be precisely quantified by generating a standard curve for the protease/indicator combination in which the rate of change in fluorescence produced by protease solutions of known activity is determined.

While detection of the fluorogenic compounds is preferably accomplished using a fluorometer, detection may by a variety of other methods well known to those of skill in the art. Thus for example, since the fluorophores of the present invention emit in the visible wavelengths, detection may be simply by visual inspection of fluorescence in response to excitation by a light source. Detection may also be by means of an image analysis system utilizing a video camera interfaced to an digitizer or other image acquisition system. Detection may also be by visualization through a filter as under a fluorescence microscope. The microscope may just provide a signal that is visualized by the operator. However the signal may be recorded on photographic film or using a video analysis system. The signal may also simply be quantified in realtime using either an image analysis system or simply a photometer.

Thus, for example, a basic assay for protease activity of a sample will involve suspending or dissolving the sample in a buffer (at the pH optima of the particular protease being assayed), adding to the buffer one of the fluorogenic protease indicators of the present invention, and monitoring the resulting change in fluorescence using a spectrofluorometer. The spectrofluorometer will be set to excite the donor fluorophore at the excitation wavelength of the donor fluorophore and to detect the resulting fluorescence at the emission wavelength of the donor fluorophore.

In another embodiment, the protease activity indicators of the present invention may be utilized for detection of protease activity in biological samples. Thus, in a preferred embodiment, this invention provides for methods of detecting protease activity in isolated biological samples such as sputum, blood, blood cells, tumor biopsies, and the like, or in situ, in cells or tissues in culture, or in section where the section is unimbedded and unfixed.

a) Ex vivo assays of isloated biological samples

In one embodiment, the present invention provides for methods of detecting protease activity in an isolated biological sample. This may be determined by simply contacting the sample with a fluorogenic protease indicator of the present invention and monitoring the change in fluorescence of the indicator over time. The sample may be suspended in a "digestion buffer" as described above. The sample may also be cleared of cellular debris, e.g. by centrifugation before analysis.

Where the fluorogenic protease indicator is bound to a solid support the assay may involve contacting the solid support bearing the indicator to the sample solution. Where the indicator is joined to the solid support by the side of the molecule bearing the donor fluorophore, the fluorescence of the support resulting from digestion of the indicator will then be monitored over time by any of the means described above. Conversely, where the acceptor molecule fluorophore is bound to a solid support, the test solution may be passed over the solid support and then the resulting luminescence of the test solution (due to the cleaved fluorophore) is measured. This latter approach may be particularly suitable for high throughput automated assays.

b) In situ assays of histological sections.

In another embodiment, this invention provides for a method of detecting in situ protease activity in histological sections. This method of detecting protease activity in tissues offers significant advantages over prior art methods (e.g. specific stains, antibody labels, etc.) because, unlike simple labeling approaches, in situ assays using the protease indicators indicate actual activity rather than simple presence or absence of the protease. Proteases are often present in tissues in their inactive precursor (zymogen) forms which are capable of binding protease labels. Thus traditional labeling approaches provide no information regarding the physiological state, vis a vis protease activity, of the tissue.

The in situ assay method generally comprises providing a tissue section (preferably a frozen section), contacting the section with one of the fluorogenic protease indicators of the present invention, and visualizing the resulting fluorescence. Visualization is preferably accomplished utilizing a fluorescence microscope. The fluorescence microscope provides an "excitation" light source to induce fluorescence of the "donor" fluorophore. The microscope is typically equipped with filters to optimize detection of the resulting fluorescence. Thus, for example, for the fluorogenic protease indicators described in Example 1, a typical filter cube for a Nikon microscope would contain an excitation filter ($\lambda=550\pm12$ nm), a dichroic mirror ($\lambda=580$ nm) and an interference-emission filter ($\lambda=580\pm10$ nm). As indicated above, the microscope may be equipped with a camera, photometer, or image acquisition system.

The sections are preferably cut as frozen sections as fixation or embedding will destroy protease activity in the sample.

The fluorogenic indicator may be introduced to the sections in a number of ways. For example, the fluorogenic protease indicator may be provided in a buffer solution, as described above, which is applied to the tissue section. Alternatively, the fluorogenic protease indicator may be provided as a semi-solid medium such as a gel or agar which is spread over the tissue sample. The gel helps to hold moisture in the sample while providing a signal in response to protease activity. The fluorogenic protease indicator may also be provided conjugated to a polymer such as a plastic film which may be used in procedures similar to the development of Western Blots. The plastic film is placed over the tissue sample on the slide and the fluorescence resulting from cleaved indicator molecules is viewed in the sample tissue under a microscope.

Typically the tissue sample must be incubated for a period of time to allow the endogenous proteases to cleave the fluorogenic protease indicators. Incubation times will range from about 10 to 60 minutes at temperatures up to and including 37° C.

In situ Assays of cells in culture.

In yet another embodiment, this invention provides for a method of detecting in situ protease activity of cells in culture. The cultured cells are grown either on chamber slides or in suspension and then transferred to histology slides by cytocentrifugation. The slide is washed with phosphate buffered saline and coated with a semi-solid polymer or a solution containing the fluorogenic protease indicator. The slide is incubated at 37° C. for the time necessary for the endogenous proteases to cleave the protease indicator. The slide is then examined under a fluorescence microscope equipped with the appropriate filters as described above.

Protease Activity Detection Kits

The present invention also provides for kits for the detection of protease activity in samples. The kits comprise one or more containers containing the fluorogenie protease indicators of the present invention. The indicators may be provided in solution or bound to a solid support. Thus the kits may contain indicator solutions or indicator "dipsticks", blotters, culture media, and the like. The kits may also contain indicator cartridges (where the fluorogenic indicator is bound to the solid support by the "acceptor" fluorophore side) for use in automated protease activity detectors.

The kits additionally may include an instruction manual that teaches the method and describes use of the components of the kit. In addition, the kits may also include other reagents, buffers, various concentrations of protease inhibitors, stock proteases (for generation of standard curves, etc), culture media, disposable cuvettes and the like to aid the detection of protease activity utilizing the fluorogenic protease indicators of the present invention.

EXAMPLES

The invention is illustrated by the following examples. These examples are offered by way of illustration, not by way of limitation.

Example 1

Synthesis of Fluorogenic Molecule for Detecting Protease Activity a) Synthesis of the peptide backbone.

The amino acid sequences Asp-Ala-Ile-Pro-Nle-Ser-Ile-Pro-Cys (SEQ ID NO:42)(where $C^1$ is Asp-Ala-Ile, P is Pro-Nle-Ser-Ile (SEQ ID NO:2) and $C^2$ is Pro-Cys) and Asp-Ala-Ile-Pro-Met-Ser-Ile-Pro-Cys (SEQ ID NO:43) (where $C^1$ is Asp-Ala-Ile, P is Pro-Met-Ser-Ile (SEQ ID NO:1) and $C^2$ is Pro-Cys) were synthesized manually utilizing a t-Boc Cys-Pam resin and t-Boc chemistry using the protocol for a coupling cycle given below in Table 3. The synthesized peptides were aleprotected by treatment with hydrofluoric acid for 60 minutes under anhydrous conditions at a temperature of 4° C.

TABLE 3

Reaction steps for one coupling cycle (addition of one amino acid) for the synthesis of the peptide backbone of the fluorogenic protease inhibitors.

| Step | Process | Time (min) | # Repeats |
|---|---|---|---|
| 1 | TFA/DCM Pre-wash 15 ml, 50% (v/v) or 35% (v/v) | 2.0 | 1 |
| 2 | TFA/DCM Main Wash 15 ml, 50% (v/v) or 35% (v/v) | 28.0 | 1 |
| 3 | DCM washes, 10 ml | <0.33 | 4 |
| 4 | DIEA/DCM, 10% (v/v), 10 ml | 2.0 | 1 |
| 5 | DIEA/DCM, 10% (v/v), 10 ml | 8.0 | 1 |
| 6 | DCM washes, 10 ml | <0.33 | 5 |
| 7 | Resin wash with NMP (or DMF) | <0.33 | 5 |
| 8 | 5-fold excess t-Boc-amino acid with HOBT and DIPC in NMP or DMF | 90 to 120 | 1 |
| 9 | DCM wash | <0.33 | 1 |
| 10 | MeOH wash | <0.33 | 1 |
| 11 | DCM washes | <0.33 | 2 |
| 12 | DIEA wash | <0.33 | 1 |
| 13 | DCM washes | <0.33 | 3 |
| 14 | Ninhydrin | 5.0 | 1 |
| 15 | 3-fold excess t-Boc-amino acid/DIPC/DCM | 30 | 1 |
| 16 | MeOH wash | <0.33 | 1 |
| 17 | DCM washes | <0.33 | 5 |
| 18 | Ninhydrin test | 5 | 1 |
| 19 | Go to step 1 to couple next amino acid | | |

Crude post-HF deprotected and cleaved peptides were purified by reverse phase HPLC using a preparative $C_{18}$ column (YMC, Inc., Charlestown, N.C., U.S.A.). The solvent system utilized was water and acetonitrile containing 0.1% (v/v) trifluoroacefic acid (TFA). HPLC was performed using the following gradient at a flow rate of 10 ml/minute:

TABLE 4

| HPLC gradient for purification of the peptide backbone. | |
|---|---|
| Time (min) | % Solvent A ($H_2O$ with TFA (0.1%)) |
| 0 | 100 |
| 7 | 100 |
| 8 | 90 |
| 68 | 50 |
| 78 | 50 |

Purification of methionine-containing peptides required subjecting the peptide to reducing conditions, e.g., dithiothreitol (DTT) and heat, to reduce methionine oxide to methionine. This reductive treatment was carried out by dissolving the peptide in 150 mM sodium phosphate buffer with 1 mM DTT, pH 7.5 for 30 minutes at 60° to 80° C. The reduction could also have been carried out under a weak acidic pH with 0.03N HCL but would have required a longer heating time. The subsequently HPLC purified methionine containing peptides were found to oxidize upon sitting either in aqueous solution or lyophilized form. The oxidized peptides were found to be reducible repeating the above reducing condition.

Derivation of the peptide backbone with the fluorophore molecules.

The peptides were derivatized sequentially with donor and acceptor fluorophores. Specifically the donor fluorophore (5'-carboxytetramethylrhodamine (C2211), available from Molecular Probes, Inc. Eugene, Oreg., U.S.A.) was first covalently linked to the amino terminus of the peptide. The peptide and the probe, at a molar ratio of 3:1 peptide to probe, were dissolved in a minimal amount of solvent NMP (N-methyl pyrolidone), usually 20 to 60 μl. One molar equivalent of DIEA (diisopropyl ethyl amine) was also added to the reaction mixture. The reaction was then incubated at 37° C. with times ranging between 12 hours and 3 days. After two days an additional 1 molar equivalent of dye molecule was sometimes added. The derivatization reached nearly maximal yield by 3 days. The peptide bearing the single C2211 fluorophore was then HPLC purified as described below.

The second (acceptor) fluorophore (rhodamine X acetamide (R492)) was then coupled to the carboxyl cysteine of the peptide by a linkage between the iodoacetamide group of the fluorophore and the sulfhydryl group of the terminal cystein. This coupling was accomplished as described above for the first fluorophore.

The complete fluorogenic protease indicator was then purified by HPLC using an analytical reverse phase $C_3$ columns (2 ml void volume) from Waters Associates Inc. (Milford, Mass., U.S.A.) using the gradient shown in Table 4 running at 1 ml/minute.

TABLE 5

| HPLC gradient for purification of the peptide bearing fluorophores. | |
|---|---|
| Time (min) | % Solvent A ($H_2O$ with TFA (0.1%)) |
| 0 | 100 |
| 1 | 100 |
| 2 | 80 |
| 6 | 80 |
| 66 | 50 |

The slow reactivity of both the amino and sulfhydryl groups in coupling the fluorophores appeared to be a function of the folded structure of the peptide backbone which sterically hindered access to the peptide's reactive groups. Control experiments using irrelevant linear peptides showed considerably faster linking. The folded structure is also supported by the results reported in Examples 2 and 3. A computer energy minimization model of the peptide also indicated possible preference for the peptide to assume a folded structure rather than an open extended structure. This is due largely to the presence of the conformation determining regions containing the two proline residues.

Example 2

Alternative Synthesis of Protease Activity Indicators a. Fmoc-protected peptide backbone synthesis The amino acid sequences listed in Table 6 were synthesized manually utilizing Fmoc chemistry and 2-chlorotritylchloride resin employing the protocol for a coupling cycle given below in Table 7.

TABLE 6

| Protease indicator peptide backbones. | | | | | |
|---|---|---|---|---|---|
| | $S^1$ | $C^1$ | P | $C^2$ | $S^2$ |
| 1. | | Asp—Ala—Ile— | Pro—Nle—Ser—Ile— (SEQ ID NO:2) | Pro—Cys— | Gly—Tyr |
| 2. | | Asp—Ala—Ile— | Pro—Nle—Ser—Ile— (SEQ ID NO:2) | Pro—Lys— | Gly—Tyr |
| 3. | Lys— | Asp—Ala—Ile— | Pro—Nle—Ser—Ile— (SEQ ID NO:2) | Pro—Lys— | Gly—Tyr |
| 4. | | Asp—Aib—Thr— | Gly—Arg—Thr—Gly— | Pro—Lys— | Gly—Tyr |
| 5. | Lys— | Asp—Aib—Thr— | Gly—Arg—Thr—Gly— | Pro—Lys— | Gly—Tyr |

The synthesized peptides were cleaved from the 2-chlorotritylchloride resin with mild acid treatment (vol/vol ratio of 2:7:1 Acetic acid:Dichloromethane:Trifluoroethanol) at room temperature for 30 minutes. A 10 ml aliquot of this peptide resin cleavage solution was added to 0.1 gm of dried peptide resin. The following side chain protecting groups were used in the synthesis: t-butyl for Asp, Ser, Thr, and Tyr residues, S-trityl and S-t-butylthio for Cys residues, and t-Boc, Fmoc and 4-methyltrityl for lysine residues.

The side chain protecting groups as well as the Fmoc group on the alpha amino group of the synthesized peptide were not cleaved with this mild acid peptide resin cleavage reagent. The protected peptide containing solution was lyophilized. The lyophilized protected peptides were further treated by either 30% (v/v) TFA in dichloromethane for t-Boc deprotection, 20% (v/v) piperidine in DMF or N-methylpyrolidone for Fmoc deprotection, 1 to 5% (v/v) trifluoroacetic acid (TFA) in water, or 1% TFA/5% triisopropylsilane in DCM, for 4-methyltrityl deprotection, aqueous mercaptoethanol (10%) for S-t-Butylthio deprotection, TFA:phenol:water:thioanisol:ethanedithiol=85:5:5:2.5:2.5 for t-Butyl, t-Boc and S-Trityl deprotection, and TFA:phenol:water=90:5:5 for t-Butyl and t-Boc deprotection.

Fully or partially side-chain deprotected peptides were purified by reversed phase HPLC using a C18 column with a water/acetonitrile gradient containing 0.075% (v/v) TFA in each solvent.

b. Derivation of the protected peptide backbone with flurophores.

The fully purified protected peptide was further treated with the appropriate reagents for selective deprotection of the side chains of Cys or Lys residues. The use of three different protecting groups, i.e., t-Boc, Fmoc, and 4-methyltrityl group, for the epsilon (ε) amino group protection of lysine, allowed selective deprotection, and thus, selective derivatization of a specific lysine residue.

For example, about 1 mg of protected peptide was dissolved in a minimal amount of N-Methylpyrolidone. The appropriate fluorophore derivatized with a succimidyl ester reactive functional group was added to the peptide solution at a 1.2 to 2 fold molar excess of reactive fluorophore over the peptide. A ten-fold mole excess of diisopropylethylamine (DIEA) was also added to the reaction mixture. The reaction was allowed to proceed at room temperature for 2 to 4 hours. The derivatized peptides were purified by reversed phase HPLC using a C18 or C4 column and 0.075% (v/v) TFA-containing water/acetonitrile solvent system.

The derivatization of the peptide with the first fluorophore was facilitated by the presence of at least one very hydrophoic group such as Fmoc. The presence of such a hydrophobic group on the peptide allowed elution (e.g. partitioning) of the derivatized peptide away from fluorophore contaminants and reaction by-products and degradation products that accumulate as the derivatization reaction is allowed to proceed.

Deprotection of the Fmoc group was then carried out after one amino group or sulfhydryl group was derivatized with the desired fluorophore. The fluorophores utilized for the amino group conjugation were C1171, 5-(and 6-)carboxytetramethylrhodamine succinimidyl ester, C 1309, 5-(and 6-)carboxy-X-rhodamine succinimidyl ester, and fluororescein isothiocyanate. After deprotection, a second fluorophore was added in a manner identical to the addition of the first.

TABLE 7

Reaction steps for one coupling cycle (addition of one amino acid) for the synthesis of the peptide backbone of the fluorogenic protease substrates.

| Step | Process | Time (min) | # repeats |
|---|---|---|---|
| 1. | Wash resin with DCM. | 1 | 1 |
| 2. | Wash resin with DMF. | 1 | 2 |
| 3. | 20% piperidine in DMF. | 5 | 1 |
| 4. | 20% piperidine in DMF. | 15 | 1 |
| 5. | Wash resin with DCM. | 1 | 4 |
| 6. | Wash resin with NMP. | 1 | 2 |
| 7. | Preactivate 2 to 4 fold mole excess Fmoc-aa, PyBoP, HoBt, and N-methylmorpholine in NMP. | 5 | 1 |
| 8. | Add the above pre-activated Fmoc-AA coupling mixture. | 45 | 1 |

TABLE 7-continued

Reaction steps for one coupling cycle (addition of one amino acid) for the synthesis of the peptide backbone of the fluorogenic protease substrates.

| Step | Process | Time (min) | # repeats |
|---|---|---|---|
| 9. | Wash resin with DCM. | 1 | 4 |
| 10. | Wash resin with methanol. | 1 | 1 | e. Molecular weight characterization of the derivatized peptides.

Since during, or after, the derivatization of the protected peptides a strong acid deprotection step was sometimes used to remove the remaining t-Butyl groups from the various amino acid side chains, there was a possibility that either aromatic amino acids or fluorophores might have been chemically modified. The molecular weights of the derivatized and purified peptides were therefore determined.

Molecular weights were measured using a matrix assisted laser desorption time of flight mass spectrometer, Kompact MADLI I by Kratos Analytical. The Mass spectometer was calibrated with Leucine-Enkaphelin (556.6 amu), Bradyldnin (1061.2 amu), and Mellitin (2847.5 amu). The sample matrix used was α-cyano-4-hydroxycinnamic acid. Samples were applied to target and 1 ml 0.1% TFA in ethanol solution was added on the target and then dried down. Cumulative mass spectral data from 50 laser shots were collected and a peak corresponding to the parent mass peak plus 1 for each sample was determined. The results are summarized on Table 8.

The good agreement between the calculated and experimentally determined mass values indicates the absence of any side reaction products in the final purified fluorophore-conjugated peptides.

TABLE 8

Calculated and determined molecular mass of the derivatized peptide protease substrates. The vertical and horizontal line indicate the fluorophore's attachment site. The symbols FL, C1171 and C1309 denote fluorophores fluoroscein isothionate, 5-(and-6)-carboxy-tetramethylrhodamine succinimidyl ester, and 5-(and-6)-carboxy-X-rhodamine succinimidyl ester, respectively. ND denotes not determined.

| | Compound | Calculated Mass (amu) | Observed Mass (amu) |
|---|---|---|---|
| 1. | C1171-DAIP(Nle)SIPKGY<br>    \|__ C1309 (SEQ ID NO: 44) | 2101.2 | 2102.6 |
| 2. | C1309-DAIP(Nle)SIPKGY<br>    \|__ C1171 (SEQ ID NO: 45) | 2101.2 | 2097.8 |
| 3. | C1171-DAIP(Nle)SIPKGY<br>    \|__ C1171 (SEQ ID NO: 46) | 1997.0 | 1997.6 |
| 4. | DAIP(Nle)SIPKGY<br>    \|__ C1309 (SEQ ID NO: 47) | 1688.7 | 1685.9 |
| 5. | C1309-DAIP(Nle)SIPKGY (SEQ ID NO: 48) | 1688.7 | 1688.1 |
| 6. | DAIP(Nle)SIPKGY<br>    \|__ C1171 (SEQ ID NO: 49) | 1585.5 | 1585.8 |
| 7. | C1171-DAIP(Nle)SIPKGY (SEQ ID NO: 50) | 1585.5 | 1583.7 |

TABLE 8-continued

Calculated and determined molecular mass of the derivatized peptide protease substrates. The vertical and horizontal line indicate the fluorophore's attachment site. The symbols Fl, C1171 and C1309 denote fluorophores fluoroscein isothionate, 5-(and-6)-carboxy-tetramethylrhodamine succinimidyl ester, and 5-(and-6)-carboxy-X-rhodamine succinimidyl ester, respectively. ND denotes not determined.

| | Compound | Calculated Mass (amu) | Observed Mass (amu) |
|---|---|---|---|
| 8. | Fl-DAIP(Nle)SIPKGY<br>      ┆__Fl (SEQ ID NO: 51) | | ND |
| 9. | C1309-DAIP(Nle)SIPKGY<br>      ┆__C1309 (SEQ ID NO: 52) | | ND |
| 10. |      KDAIP(Nle)SIPKGY<br>C1171__┆          ┆__C1309 (SEQ ID NO: 53) | | ND |
| 11. |      KDAIP(Nle)SIPKGY<br>C1171__┆          ┆__C1171 (SEQ ID NO: 54) | | ND |

Example 3

The Fluorogenic Protease Indicators Provide a Strong Signal When Digested

In order to demonstrate that the fluorogenic protease indicators of this invention are easily digested by a protease, the degree of cleavage was determined by assaying for the appearance of indicator cleavage products in the presence of a protease.

Approximately 1 microgram of protease indicator, having the formula $F^1$-Asp-Ala-Ile-Pro-Nle-Ser-Ile-Pro-Cys-$F^2$ (SEQ ID NO:40) where $F^1$ is a donor fluorophore (5'-carboxytetramethylrhodamine (C2211)) linked to aspartic acid via the alpha amino group and $F^2$ is an acceptor fluorophore (rhodamine X acetamide (R492)) linked via the sulfhydryl group of the cysteine was dissolved in a buffer consisting of 50 mM sodium phosphate, 1 mM EDTA at pH 8.9. To this solution was added 1 unit of elastase. The solution was analyzed by HPLC before and about 30 minutes after the addition of elastase. The digestion was carried out at 37° C. The HPLC separated components were monitored at a wavelength of 550 nm which allowed detection of both the C2211 fluorophore the R492 fluorophore and at 580 nm which allowed detection of the R492 fluorophore.

Figure 1B:
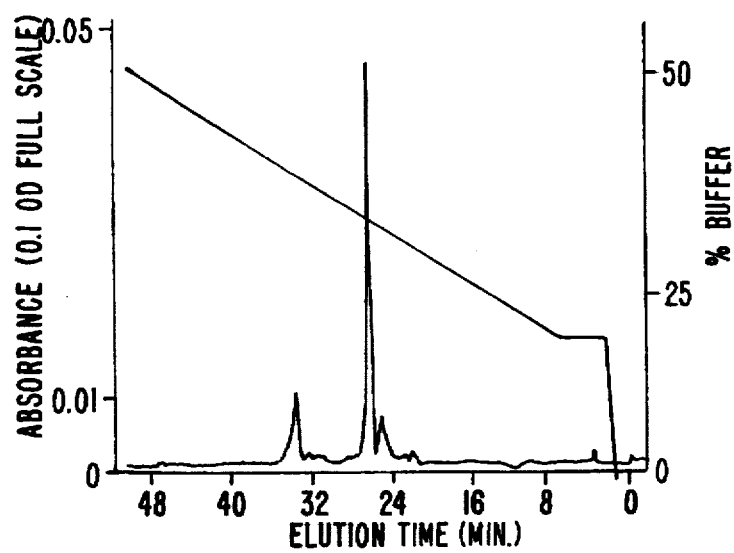
Figure 1C:
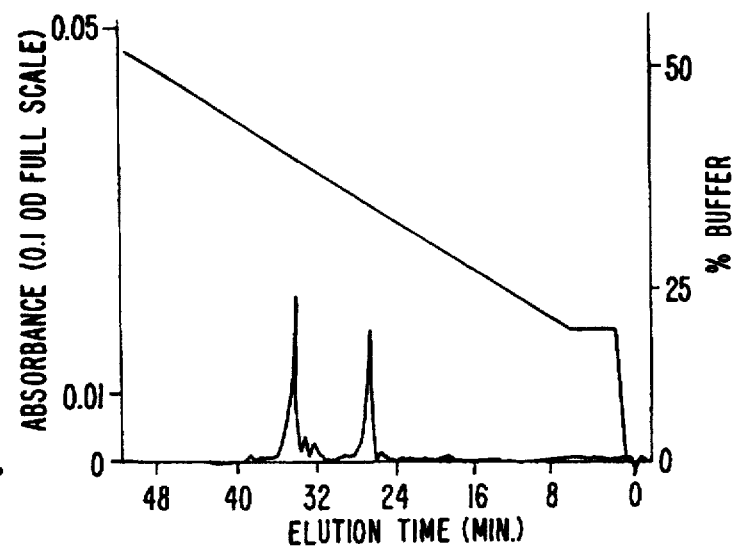

The results are indicated in FIG. 1 which shows the HPLC profiles of the fluorogenic protease indicator solution before and after addition of the protease elastase. FIG. 1(a) shows the HPLC before addition of the elastase showing a single peak representing the intact fluorogenic protease inhibitor. After addition of the elastase (FIGS. 1(b) and 1(c)) there was no trace of the late eluting single peak (FIG. 1(a)) indicating complete digestion of the fluorogenic protease indicator. In addition, the two predominant peaks in FIGS. 1(b) and 1(c) indicate that the digestion occurred primarily at a single site. There are a few smaller peaks indicating a low degree of digestion at other sites within the peptide sequence, however, the striking predominance of only two digestion peaks suggests that these secondary sites were not readily accessible to the elastase.

Changes in the emission spectrum of the fluorogenic protease indicator after the addition of an elastase protease was monitored using an SLM spectrofluorometer model 48000 with slit widths set at 4 nm on both the excitation and emission sides. All measurements were carried out at 37° C.

Figure 2A:
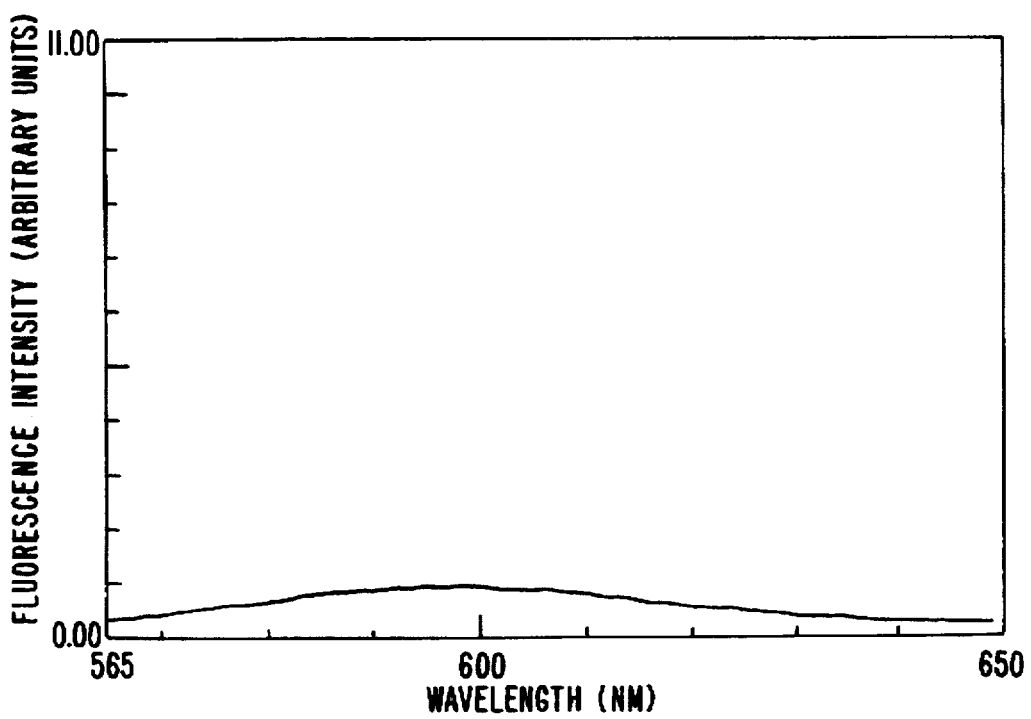
FIG. 2 shows the emission spectra of the D-NorFES-A fluorogenic protease indicator (a) before and (b) after the addition of elastase.
Figure 2B:
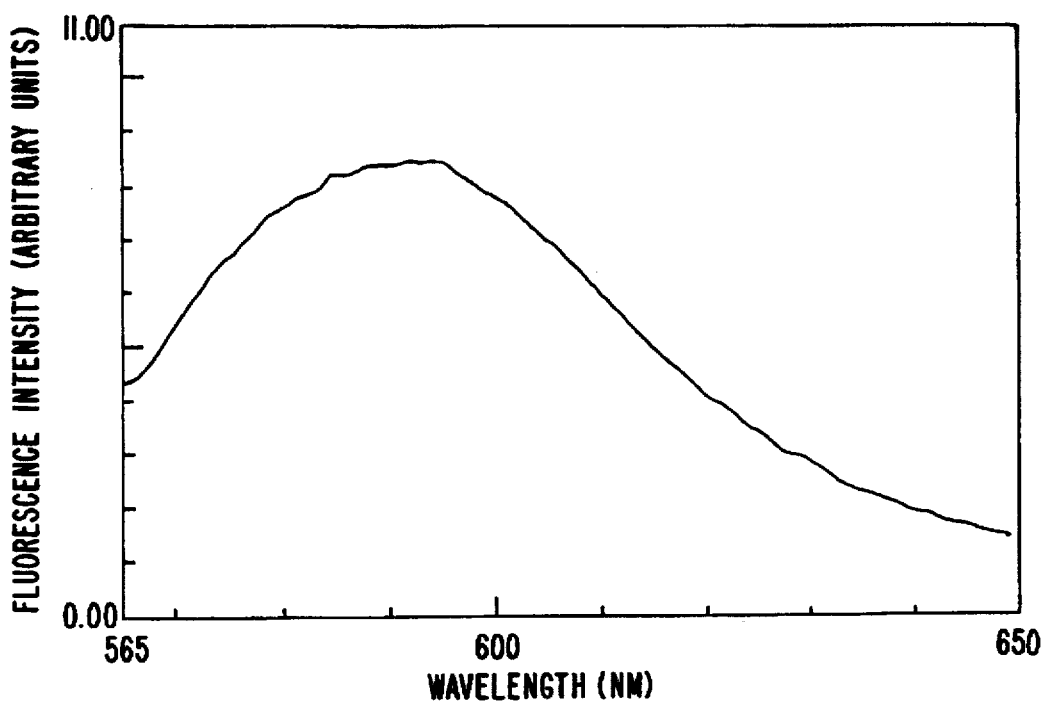
Figure 3:
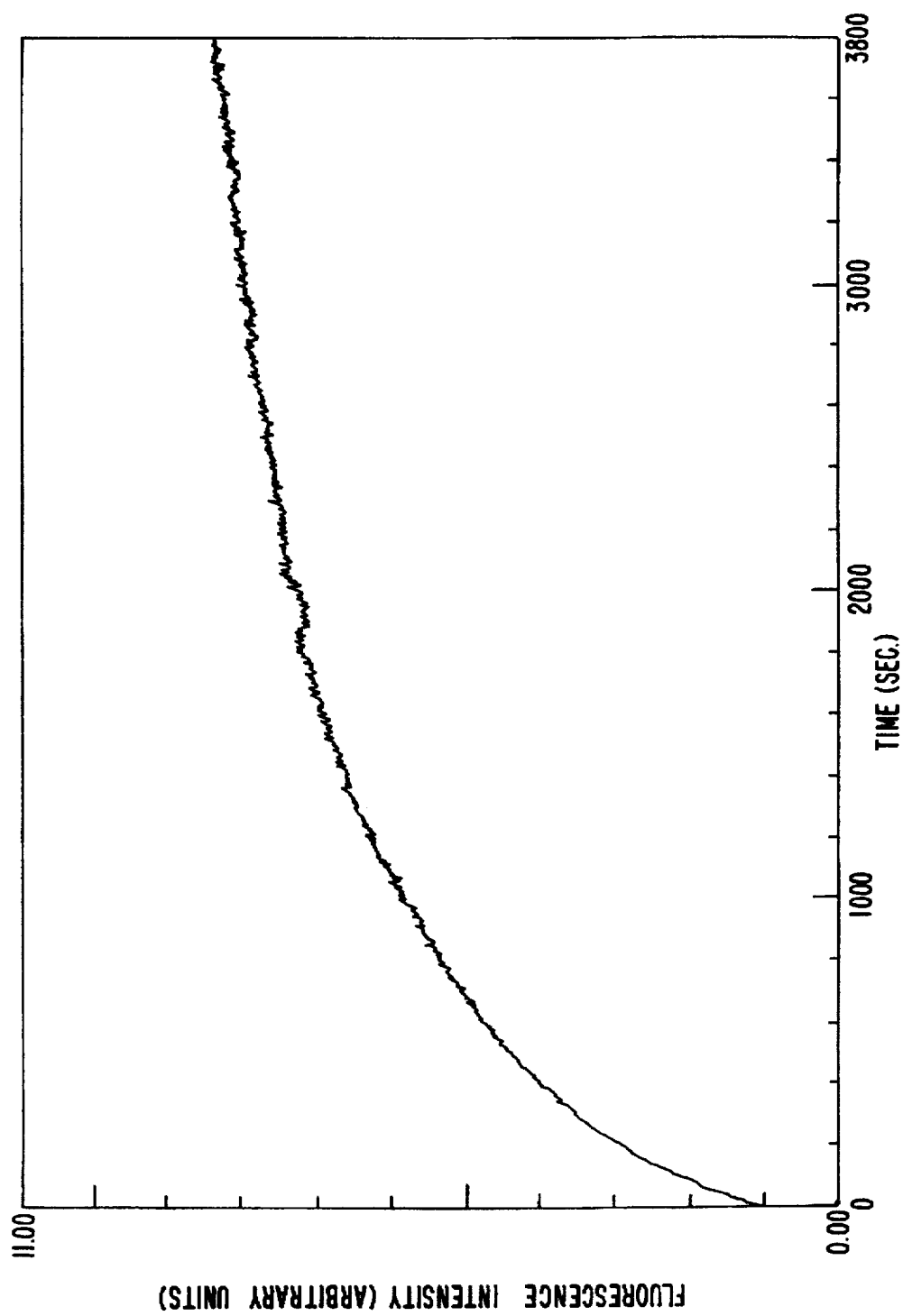
FIG. 3 shows the time-dependent increase of the fluorogenic protease indicator of FIG. 1, as a function of time after addition of 1 unit of elastase.

Spectra in FIG. 2 show emission of the fluorogenic protease indicator (a) before and (b) after addition of elastase, while the time dependent increase of the indicator's donor fluorophore emission intensity, after addition of elastase, is plotted in FIG. 3. The fluorogenic protease inhibitor showed more than a 10 fold increase in fluorescence at 589 nm after treatment with the elastase protease (FIG. 2(a) compared to FIG. 2(b)) with over a 5 fold increase in fluorescence occurring within the first 1000 seconds of exposure to the protease. The changes in intensity between treated and untreated indicators are, to some degree, a function of slit widths used, since they represent the signal integrated across the particular slit width. Thus, if wider slit widths were used (e.g. 8 or 16 nm slits) an even greater signal would be provided in response to digestion.

Example 4

The Fluorescence Signal Was Due to Intramolecular Energy Dequenching

In order to show that the fluorescence increase observed after protease treatment was due to intramolecular energy dequenching, the signal produced by elastase digestion of the fluorogenic protease indicator was compared to the signal produced by elastase treatment of the same peptide backbone coupled to either $F^1$ (C2211) or to $F^2$ (R492). The change in fluorescence intensity of the donor fluorophore after addition of 1 unit of elastase to equal concentrations of the double-fluorophore molecule and the two single-fluorophore molecules.

Figure 4A:
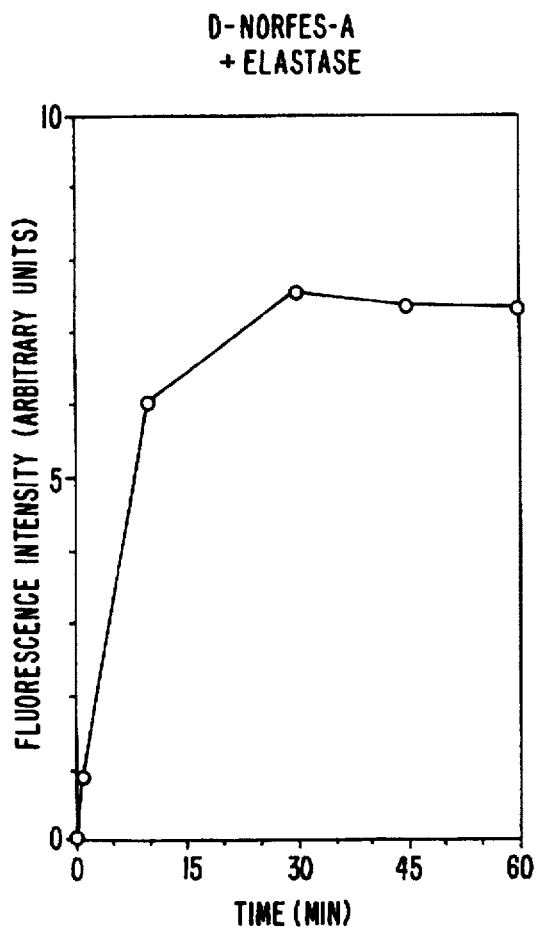
FIG. 4 shows the fluorescence intensity of the donor fluorophore as a function of time after addition of 1 unit of elastase. (a) The fluorogenic protease indicator of FIG. 1. (b) The peptide backbone of the fluorogenic protease of FIG. 1 singly labeled with each of the two fluorophores. D-NorFES-A is the $F^1$-Asp-Ala-Ile-Pro-Nle-Ser-Ile-Pro-Cys-$F^2$ protease indicator where $F^1$ is a donor fluorophore (5'-carboxytetramethylrhodamine (C2211) and $F^2$ is an acceptor fluorophore (rhodamine X acetamide (R492). D-NorFES and A-NorFES each designate a molecule having the same peptide backbone, but bearing only one of the two fluorophores.
Figure 4B:
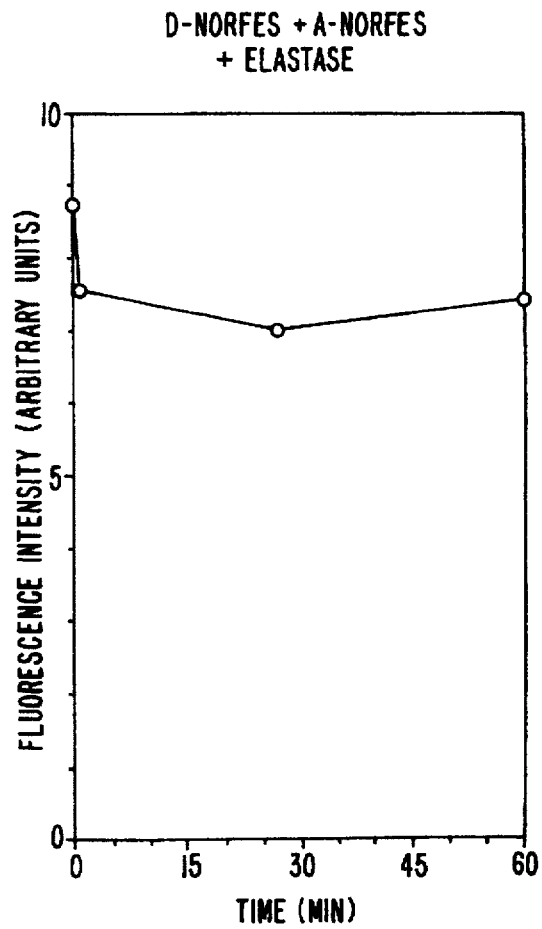

The results are illustrated in FIG. 4. The double-fluorophore molecule showed nearly complete quenching initially, followed by a dramatic increase in fluorescence after addition of the elastase which reached a constant value approximately 30 minutes after addition of the elastase (FIG. 4(a)). In contrast, the two single-fluorophore molecules showed virtually no initial quenching and no significant change in fluorescence after addition of the elastase. In fact, the fluorescence level was comparable to the fluorescence level of the fully digested double-fluorophore indicator molecule (FIG. 4(b)).

These results indicate that the increase in fluorescence intensity of the fluorogenic protease indicator is due to interruption of the resonance energy transferred intramolecularly from the donor fluorophore to the acceptor fluorophore and not to interaction between the fluorophore and the peptide backbone. This is significant since it is known that upon binding to a large protein or hydrophobic peptide the fluorescence of many hydrophobic fluorophores is quenched.

Example 5

Without being bound to a particular theory, it is believed that the fluorogenic protease indicators of the present invention achieve a high degree of protease specificity due to their folded structure, more particularly due to their relative rigid U-shaped conformation. The fluorescence obtained from the molecule reflects the average separation of two fluorophores. Thus, it was predicted that if the protease indicators existed in a relatively unfolded or flexible state, conditions that tend to cause unfolding (denaturation) would have little or no effect on the fluorescence of the molecule in the absence of a protease. Conversely, if the molecule is relatively rigid, then denaturing conditions would be expected to increase the fluorescence signal as the average separation of the fluorophores would be expected to increase thereby decreasing the quenching effect.

Thus, the effect of denaturing conditions on the fluorescence of the fluorogenic protease indicator in the absence of a protease was determined. First the change of fluorescence of the indicator of Example 1, as a function of temperature, was measured. Relative fluorescence intensity (of the donor fluorophore) increased approximately linearly from a value of about 0.6 (relative fluorescence units (RUs)) at 25° C. to a value of about 1.2 RUs at 50° to 55° C. and thereafter reached a plateau.

Similarly when denatured with a chaotropic reagent (2M or 8M urea) the fluorescence intensity increase with time to a plateau as the molecule denatured (unfolded).

These data indicate that the fluorogenic protease indicator normally exists in a stable folded conformation created by the conformation determining regions, as was predicted by a model based on an energy minimization algorithm. The plateau fluorescence level represents residual quenching of the fluorophores still joined by the fully denatured peptide backbone. Digestion of the extended (denatured) peptide results in greater than a 2 fold increase in fluorescence as the fluorophores are able to move farther away from each other.

Example 6

Quenching and Release of Peptide Doubly-Labeled with One Fluorophore

It was a surprising discovery of this invention that the peptide backbones of this invention doubly labeled with one fluorophore still achieve fluorescence quenching thus suggesting quenching through another mechanism besides resonance energy transfer.

In order to assess the extent ground-state dimerization and collisional quenching contribute to the total observed quenching, the series of doubly-labeled peptides listed in Table 9 was synthesized.

In addition to comparing absorption spectra of the dyes alone with the NorFes peptides singly labeled with each dye, emission spectra taken before and after cleavage were compared to determine the percent of quenching and the existence of fluorescent signal quenching by means other than resonance energy transfer (RET).

Fluorophores were linked to the amino terminus via the a-amino group of Aspartic acid residue (D) and to the ε-amino group of lysine (K). Labeling was accomplished by the displacement of a succinimidyl group linked to C1171 or C1309. The structure of the peptide, called NorFES-KGY is:

Fluorophore1-DAIPNleSIPKGY          (SEQ ID NO:55)
                   |
                     Fluorophore2

As determined from absorption spectroscopy, all doubly-labeled peptides, except fluorescein-NorFES-fluorescein, showed the existence of so called ground-state dimers. This was indicated by shift of absorption maxima to shorter wavelengths as well as a shape change of the absorption spectra as compared with the spectra for the enzyme digested doubly-labeled samples. Upon cleavage with elastase, the ground-state dimers were destroyed and the resulting spectra were the same as a solution containing equal concentrations of the respective singly labeled peptides.

Without being bound to a particular theory, it is believed that the ground-state dimer formation observed in the compounds designed and synthesized according to the present invention indicates that the U-shaped conformation of the peptide backbone brings the fluorophores into close spatial proximity thus allowing overlap of electron orbitals of the two fluorophores resulting in reciprocal quenching through ground-state dimerization. It was a surprising discovery that the polypeptides of this invention allowed the formation of ground-state dimers at a significantly lower dye concentration than previously observed. For example, ground-state dimerization of free fluorescein dye in solution was only observed at concentrations higher than than 0.74M, ground-state dimerization of free Eosin dye in solution was only observed at concentrations higher than $2.8 \times 10^{-2}$M (see, Forster and Konig, *Zeitschrift fur Electrochemie*, 61: 344 (1957)), and ground-state dimerization of Rhodamine B dye in solution was only observed at concentrations higher than $6 \times 10^{-4}$M (see Arbeloa and Ojeda, *Chemical Physics Letters*, 87: 556 (1982)). In contrast, in the present invention, the effects are observed at $4.0 \times 10^{-7}$M or about a 1000 fold lower concentration than the reported values.

The observation of the ground-state dimer for the compounds synthesized according to the present invention predicted a significant level of fluorescent quenching for doubly-labeled peptide with the same fluorophore as those compounds listed in Table 9. In fact this prediction was confirmed; a comparison of C1171-NorFES-KGY-C1309 with C1171-NorFES-KGY-C 1171, i.e., the hetero doubly-labeled with the homo doubly-labeled peptides, indicates the degree of quenching is slightly higher in the hetero- vs. the homo- (94 vs. 90%). The fluorescein derivative, however, exhibited only 55% quenching. The symbols $I_0$ and $I_c$ for the percent fluorescent quenching (% Q) refer to the fluorescence intensity for the intact labeled peptide and the enzyme digested labeled peptide solution respectively.

TABLE 9

Cleavage rate ($T_{1/2}$) and percentage of quenching (% Q) of hetero- and homo-labeled peptides. $T_{1/2}$ is the time in seconds after addition of a protease (e.g. elastase) at which the fluorescence signal is ½ maximum.
The symbols $I_o$ and $I_c$ refer to the fluorescence intensity (I) for the intact labeled peptide and the enzyme digested labeled peptide solution respectively.

| Compound | $T_{1/2}$ | % Q = (1 − ($I_c/I_o$)) × 100 |
|---|---|---|
| C1171-NorFes-C1309 | 80 | 94 |
| C1171-NorFes-C1171 | 44 | 90 |
| C1171-NorFes-C1171 | 44 | 90 |

TABLE 9-continued

Cleavage rate ($T_{1/2}$) and percentage of quenching (% Q) of hetero- and homo-labeled pepfides. $T_{1/2}$ is the time in seconds after addition of a protease (e.g. elastase) at which the fluorescence signal is ½ maximum. The symbols $I_o$ and $I_c$ refer to the fluorescence intensity (I) for the intact labeled peptide and the enzyme digested labeled peptide solution respectively.

| Compound | $T_{1/2}$ | % Q = (1 − ($I_c/I_o$)) × 100 |
|---|---|---|
| C1309-NorFes-C1309 | 152 | 90 |
| F1-NorFes-F1 | 18 | 55 |
| C1171-NorFes-C1309 | 80 | 94 |
| C1171-K-NorFes-C1309 | 125 | 97 |
| C1171-NorFes-C1171 | 44 | 90 |
| C1171-K-NorFes-C1171 | 84 | 92 |

The substrate sequence could be extended by one amino acid residue and the fluorophore could be attached through the episilon amino group on the lysine residue's side chain without major perturbation to the amount of observed quenching. Specifically, this addition (peptides designated K-NorFES-KGY) resulted in a slight decrease in cleavability rate and a very slight increase in the percent quenching for both the hetero- and homo-doubly-labeled peptide (in the K-NorFES-KGY peptides, N-terminal labeling was via the epsilon-amino group of lysine rather than the α-amino terminus).

Rates of cleavage ($T_{1/2}$) of these substrates by elastase were also measured by recording the time after addition of the protease at which the signal was one-half maximum (see, Table 9). A comparison of three homo-doubly-labeled peptides, i.e., NorFES-KGY labeled with two molecules of C1171, C1309, and fluorescein (F1), shows the order of cleavability to be: F1-NorFES-KGY-F1>C1171-NorFES-KGY-C1171>C1309-NorFES-KGY-C1309.

Example 7

Use of Homo-Doubly Labeled Prostease Indicators

In order to demonstrate the efficacy of the protease indicators of this invention in vitro, cells of the epidermal carcinoma cell line, A431, were grown to incomplete confluence in a Permanox tissue culture chamber slide (Nunc, Inc., Naperville, Ill., U.S.A.) in Dulbecco's Minimal Essential Medium (DME) containing 5% fetal calf serum (FCS). After removal of the medium, 200 μl of a solution containing 70% ethanol was added to each chamber and incubation was carried out for two minutes. The ethanolic medium was then removed and the monolayers were washed twice with DME (minus the FCS).

A DME solution containing C1171-NorFes-C1171 at a concentration of $1×10^{-7}M$ was then incubated with the monolayer for 10 minutes. The cells were then examined for fluorescence with a Nikon fluorescence microscope using a rhodamine filter cube. (An advantage of using peptides homo-doubly-labeled with a single fluorophore compared to those labeled with two different fluorophores [hetero-doubly-labeled] is that fluorescence microscopy using homo-doubly-labeled peptides only requires a cutoff filter [i.e., a filter that transmits all light above a defined wavelength] on the emission side of the dichroic mirror, whereas fluorescence microscopy using hetero-doubly-labeled peptides preferably uses an interference filter [i.e., a filter that transmits light in a defined wavelength range (x±y nm)]).

Each cell was clearly defined by a diffuse red fluorescence (produced by the protease indicator cleaved by elastase) filling its entire cytoplasm. For cells at the edge of a confluent island, the black borders of the islands were clearly distinct from the red fluorescence in the cytoplasm of the cells indicating that the fluorescence was not due to background fluorescence or to cleavage of the protease indicator by the medium.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

---

What is claimed is:

1. A fluorogenic composition for the detection of the activity of a protease, said composition having the formula:

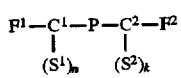   I wherein,

P is a peptide comprising a protease binding site for said protease, said binding site consisting of about 2 to about 8 amino acids;

$F^1$ and $F^2$ are fluorophores;

$S^1$ and $S^2$ are peptide spacers ranging in length from 1 to about 50 amino acids;

n and k are independently 0 or 1; and $C^1$ and $C^2$ are conformation determining regions comprising peptides ranging in length from 1 to about 3 amino acids, said conformation determining regions positioning said fluorophores adjacent to each other with a separation of less than about 100 Å; and when n is 1, $S^1$ is joined to $C^1$ by a peptide bond through a terminal alpha amino group of $C^1$; and when k is 1, $S^2$ is joined to $C^2$ by a peptide bond through a terminal alpha carboxyl group of $C^2$.

2. The composition of claim 1, wherein P is a tetrapeptide, $C^1$ is a tripeptide and $C^2$ is an amino acid or a dipeptide, said composition having the formula:

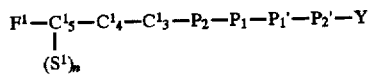   II wherein $C^1_5$, $C^1_4$, $C^1_3$, $P_2$, $P_1$, $P_1'$, $P_2'$ are amino acids; and Y is a composition selected from the group consisting of compounds of formulas:

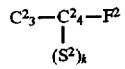   III and

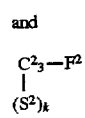   IV wherein $C^2_3$ and $C^2_4$ are amino acids; and when $P_2'$ is not a proline then Y is formula III in which $C^2_3$-$C^2_4$ is selected from the group consisting of Pro-Cys, Aib-Cys, Pro-Lys, and Aib-Lys;

when $P_2'$ is a proline Y is formula IV in which $C^2_3$ is selected from the group consisting of Cys and Lys;

when $P_2$ is a proline then $C^1_5$-$C^1_4$-$C^1_3$ is Asp-$C^1_4$-$C^1_3$, or Asp-$C^1_4$-Aib; and when $P_2$ is not a proline then $C^1_5$-$C^1_4$-$C^1_3$ is selected from the group consisting of Asp-$C^1_4$-Pro, Asp-$C^1_4$-Aib, Asp-Aib-Pro, Asp-Pro-$C^1_3$, Asp-Aib-$C^1_3$, Asp-Pro-Aib and Asp-Aib-Aib.

3. The composition of claim 2, wherein $P_2$ is selected from the group consisting of Pro, Gly, Phe, Arg, Leu, Gln, Glu, Ile, His, and Ala;

$P_1$ is selected from the group consisting of Cys, Met, Nle, Arg, Leu, Gly, His, Glu, Ala, Phe, Tyr, and Asn;

$P_1$ is selected from the group consisting of Thr, Ser, Met, Nle, Leu, Ala, Ile, Phe, Val, Glu, His, and Tyr; and $P_2'$ is selected from the group consisting of Ile, Gly, Met, Nle, Leu, Ala, Gln, Arg, Val, Ser, Tyr, Gln, and Asn.

4. The composition of claim 2, wherein $C^1_5$ is Asp;

$C^1_4$ is selected from the group consisting of Ala, Met, Nle, Aib, Pro, Ile, Gly, Asp, Arg, Thr, Phe, Lys, Gln, and Ser;

$C^1_3$ is selected from the group consisting of Ile, Aib, Pro, Thr, Ser, Ala, Val, Gly, Phe, and Gln.

5. The composition of claim 2, wherein $P_2'$ is Pro;

Y is Formula IV;

$C^2_3$ is selected from the group consisting of Cys and Lys.

6. The composition of claim 2, wherein

Y is Formula III; and $C^2_3$-$C^2_4$ is selected from the group consisting of Pro-Cys, and Pro-Lys.

7. The composition of claim 2, wherein k is 1; and $S^2$ is Gly-Tyr.

8. The composition of claim 1, wherein $F^1$ is a fluorophore having an excitation wavelength ranging from about 315 nm to about 650 nm.

9. The composition of claim 1, wherein $F^2$ is a fluorophore having an excitation wavelength ranging from about 315 nm to about 650 nm.

10. The composition of claim 1, wherein $F^1$ is selected from the group consisting of 5-carboxytetramethylrhodamine and 7-hydroxy-4-methylcoumarin-3-acetic acid.

11. The composition of claim 1, wherein $F^2$ is selected from the group consisting of rhodamine X acetamide and 7-diethylamino-3-((4'-iodoacetyl)amino)phenyl)-4-methylcoumarin.

12. The composition of claim 1, wherein $F^1$ and $F^2$ are the same.

13. The composition of claim 12, wherein $F^1$ and $F^2$ are selected from the group consisting of fluoroscein isothionate, 5-(and-6)-carboxytetramethylrhodamine succinimidyl ester, and 5-(and-6)-carboxy-X-rhodamine succinimidyl ester.

14. The composition of claim 1, wherein n and k are 0;

$C^1$ is Asp-Ala-Ile;

P is Pro-Nle-Ser-Ile (SEQ ID No:2);

$C^2$ is Pro-Cys;

$F^1$ is 5-carboxytetramethylrhodamine; and $F^2$ is rhodamine X acetamide.

15. The composition of claim 1, wherein n and k are 0;

$C^1$ is Asp-Ala-Ile;

P is Pro-Met-Ser-Ile (SEQ ID NO:1);

$C^2$ is Pro-Cys;

$F^1$ is 5-carboxytetramethylrhodamine; and $F^2$ is rhodamine X acetamide.

16. The composition of claim 1, wherein n is 0;

k is 1;

$C^1$ is Asp-Ala-Ile;

P is Pro-Nle-Ser-Ile (SEQ ID No:2);

$C^2$ is selected from the group consisting of Pro-Cys, and Pro-Lys; and $S^2$ is Gly-Tyr.

17. The composition of claim 1, wherein n is 1;

k is 1;

$C^1$ is Asp-Ala-Ile;

P is Pro-Nle-Ser-Ile (SEQ ID NO:2);

$C^2$ is selected from the group consisting of Pro-Cys, and Pro-Lys;

$S^1$ is Lys; and $S^2$ is Gly-Tyr.

18. The composition of claim 1, wherein said composition is selected from the group consisting of the compositions listed in Table 8.

19. The composition of claim 1, wherein n is 1;

k is 0;

$C^1$ is Asp-Ala-Ile;

P is Pro-Nle-Ser-Ile (SEQ ID No:2);

$C^2$ is Pro-Cys; and $S^1$ is Lys-Lys-Gly-Gly-Gly (SEQ ID No:56).

20. The composition of claim 19, wherein $S^1$ is conjugated to a solid support.

21. The composition of claim 1, wherein $C^1$ is Asp-Ala-Ile;

P is Pro-Nle-Ser-Ile (SEQ ID No:2); and $C^2$ is Pro-Cys;

n is 0;

k is 1; and $S^2$ is Asp-Gly-Gly-Gly-Lys-Lys (SEQ ID No:38).

22. The composition of claim 21, wherein $S^2$ is conjugated to a solid support.

23. A method of detecting the activity of a protease in a biological sample, said method comprising the steps of:

contacting said biological sample with a fluorogenic composition having the formula:

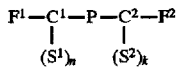   I wherein,

P is a peptide comprising a protease binding site for said protease, said binding site consisting of about 2 to about 8 amino acids;

$F^1$ and $F^2$ are fluorophores;

$S^1$ and $S^2$ are peptide spacers ranging in length from 1 to about 50 amino acids;

n, and k are independently 0 or 1; and $C^1$ and $C^2$ are conformation determining regions comprising peptides ranging in length from about 1 to about 3 amino acids, said conformation determining regions positioning said fluorophores adjacent to each other with a separation of less than about 100 Å; and when n is 1, $S^1$ is joined to $C^1$ by a peptide bond through a terminal alpha amino group of $C^1$; and when k is 1, $S^2$ is joined to $C^2$ by a peptide bond through a terminal alpha carboxyl group of $C^2$; and detecting a change in fluorescence of said fluorogenic composition wherein an increase in fluorescence indicates protease activity.

24. The method of claim 23, wherein said biological sample is selected from the group consisting of a histological section, a cultured cell, a biofluid, and a tissue.

25. The method of claim 23, wherein P is a tetrapeptide, $C^1$ is a tripeptide and $C^2$ is an amino acid or a dipeptide, said composition having the formula:

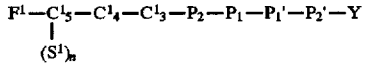   II wherein $C^1_5$, $C^1_4$, $C^1_3$, $P_2$, $P_1$, $P_1{}'$, $P_2{}'$ are amino acids; and Y is a composition selected from the group consisting of compounds of formulas:

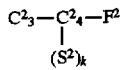

III and

IV wherein $C^2_3$ and $C^2_4$ are amino acids; and when $P_2{}'$ is not a proline then Y is formula III in which $C^2_3$-$C^2_4$ is selected from the group consisting of Pro-Cys, Aib-Cys, Pro-Lys, and Aib-Lys;

when $P_2{}'$ is a proline Y is formula IV in which $C^2_3$ is selected from the group consisting of Cys and Lys;

when $P_2$ is a proline then $C^1_5$-$C^1_4$-$C^1_3$ is Asp-$C^1_4$-$C^1_3$, or Asp-$C^1_4$-Aib; and when $P_2$ is not a proline then $C^1_5$-$C^1_4$-$C^1_3$ is selected from the group consisting of Asp-$C^1_4$-Pro, Asp-$C^1_4$-Aib, Asp-Aib-Pro, Asp-Pro-$C^1_3$, Asp-Aib-$C^1_3$, Asp-Pro-Aib and Asp-Aib-Aib.

26. The method of claim 25, wherein $P_2$ is selected from the group consisting of Pro, Gly, Phe, Arg, Leu, Gln, Glu, Ile, His, and Ala;

$P_1$ is selected from the group consisting of Cys, Met, Nle, Arg, Leu, Gly, His, Glu, Ala, Phe, Tyr, and Asn;

$P_1{}'$ is selected from the group consisting of Thr, Ser, Met, Nle, Leu, Ala, Ile, Phe, Val, Glu, His, and Tyr; and $P_2{}'$ is selected from the group consisting of Ile, Gly, Met, Nle, Leu, Ala, Gln, Arg, Val, Ser, Tyr, Gln, and Asn.

27. The method of claim 26, wherein $C^1_5$ is Asp;

$C^1_4$ is selected from the group consisting of Ala, Met, Nle, Aib, Pro, Ile, Gly, Asp, Arg, Thr, Phe, Lys, Gln, and Ser;

$C^1_3$ is selected from the group consisting of Ile, Aib, Pro, Thr, Ser, Ala, Val, Gly, Phe, and Gln.

28. The method of claim 26, wherein $P_2{}'$ is Pro;

Y is Formula IV;

$C^2_3$ is selected from the group consisting of Cys and Lys.

29. The method of claim 26, wherein

Y is Formula III; and $C^2_3$-$C^2_4$ is selected from the group consisting of Pro-Cys and Pro-Lys.

30. The method of claim 26, wherein k is 1; and $S^2$ is Gly-Tyr.

31. The method of claim 23, wherein $F^1$ is a fluorophore having an excitation wavelength ranging from about 315 nm to about 650 nm.

32. The method of claim 23, wherein $F^2$ is a fluorophore having an excitation wavelength ranging from about 315 nm to about 650 nm.

33. The method of claim 23, wherein $F^1$ is selected from the group consisting of 5-carboxytetramethylrhodamine and 7-hydroxy-4-methylcoumarin-3-acetic acid.

34. The method of claim 23, wherein $F^2$ is selected from the group consisting of rhodamine X acetamide and 7-diethylamino-3-((4'-iodoacetyl)amino)phenyl)-4-methylcoumarin.

35. The method of claim 23, wherein $F^1$ and $F^2$ are the same.

36. The method of claim 35, wherein $F^1$ and $F^2$ are selected from the group consisting of fluoroscein isothionate, 5-(and-6)-carboxytetramethylrhodamine succinimidyl ester, and 5-(and-6)-carboxy-X-rhodamine succinimidyl ester.

37. The method of claim 23, wherein n and k are 0;

$C^1$ is Asp-Ala-Ile;

P is Pro-Nle-Ser-Ile (SEQ ID No:2);

$C^2$ is Pro-Cys;

$F^1$ is 5-carboxytetramethylrhodamine; and $F^2$ is rhodamine X acetamide.

38. The method of claim 23, wherein n and k are 0;

$C^1$ is Asp-Ala-Ile;

P is Pro-Met-Ser-Ile (SEQ ID No:1);

$C^2$ is Pro-Cys;

$F^1$ is 5-carboxytetramethylrhodamine; and $F^2$ is rhodamine X acetamide.

39. The method of claim 23, wherein n is 0;

k is 1;

$C^1$ is Asp-Ala-Ile;

P is Pro-Nle-Ser-Ile (SEQ ID No:2);

$C^2$ is selected from the group consisting of Pro-Cys, and Pro-Lys; and $S^2$ is Gly-Tyr.

40. The method of claim 23, wherein n is 1;

k is 1;

$C^1$ is Asp-Ala-Ile;

P is Pro-Nle-Ser-Ile (SEQ ID No:2);

$C^2$ is selected from the group consisting of Pro-Cys, and Pro-Lys;

$S^1$ is Lys; and $S^2$ is Gly-Tyr.

41. The method of claim 23, wherein said composition is selected from the group consisting of the compositions listed in Table 8.

42. The method of claim 23, wherein n is 1;

k is 0;

$S^1$ is Lys-Lys-Gly-Gly-Gly (SEQ ID No:56);

$C^1$ is Asp-Ala-Ile;

P is Pro-Nle-Ser-Ile (SEQ ID No:2); and $C^2$ is Pro-Cys.

43. The method of claim 42, wherein $S^1$ is conjugated to a solid support.

44. The method of claim 23, wherein $C^1$ is Asp-Ala-Ile;

P is Pro-Nle-Ser-Ile (SEQ ID No:2); and $C^2$ is Pro-Cys;

n is 0;

k is 1; and $S^2$ is Asp-Gly-Gly-Gly-Lys-Lys (SEQ ID No:38).

45. The method of claim 44, wherein $S^2$ is conjugated to a solid support.

* * * * *

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

Pro  Met  Ser  Ile
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /product="Nle"

( x i ) SEQUENCE DESCRIPTION: SEQ ID NO:2:

Pro   Xaa   Ser   Ile
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

Gly   Arg   Thr   Gly
    1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:4:

Arg   Met   Ser   Leu
    1

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /product="Nle"

( x i ) SEQUENCE DESCRIPTION: SEQ ID NO:5:

Arg   Xaa   Ser   Leu
    1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS:

(D) TOPOLOGY: linear (ii) MOLECULE TYPE: peptide (xi) SEQUENCE DESCRIPTION: SEQ ID NO:6:

Gly Arg Ser Leu
1

(2) INFORMATION FOR SEQ ID NO:7:

(i) SEQUENCE CHARACTERISTICS:
 (A) LENGTH: 4 amino acids
 (B) TYPE: amino acid
 (C) STRANDEDNESS:
 (D) TOPOLOGY: linear (ii) MOLECULE TYPE: peptide (xi) SEQUENCE DESCRIPTION: SEQ ID NO:7:

Leu Leu Ala Leu
1

(2) INFORMATION FOR SEQ ID NO:8:

(i) SEQUENCE CHARACTERISTICS:
 (A) LENGTH: 4 amino acids
 (B) TYPE: amino acid
 (C) STRANDEDNESS:
 (D) TOPOLOGY: linear (ii) MOLECULE TYPE: peptide (xi) SEQUENCE DESCRIPTION: SEQ ID NO:8:

Leu Gly Ile Ala
1

(2) INFORMATION FOR SEQ ID NO:9:

(i) SEQUENCE CHARACTERISTICS:
 (A) LENGTH: 4 amino acids
 (B) TYPE: amino acid
 (C) STRANDEDNESS:
 (D) TOPOLOGY: linear (ii) MOLECULE TYPE: peptide (xi) SEQUENCE DESCRIPTION: SEQ ID NO:9:

Gln Gly Ile Leu
1

(2) INFORMATION FOR SEQ ID NO:10:

(i) SEQUENCE CHARACTERISTICS:
 (A) LENGTH: 4 amino acids
 (B) TYPE: amino acid
 (C) STRANDEDNESS:
 (D) TOPOLOGY: linear (ii) MOLECULE TYPE: peptide (xi) SEQUENCE DESCRIPTION: SEQ ID NO:10:

Gln Gly Leu Leu
1

(2) INFORMATION FOR SEQ ID NO:11:

(i) SEQUENCE CHARACTERISTICS:
 (A) LENGTH: 4 amino acids
 (B) TYPE: amino acid
 (C) STRANDEDNESS:

( D ) TOPOLOGY: linear ( i i ) MOLECULE TYPE: peptide ( x i ) SEQUENCE DESCRIPTION: SEQ ID NO:11:

Gln Gly Ile Ala
1

( 2 ) INFORMATION FOR SEQ ID NO:12:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:12:

Gln Ala Ile Ala
1

( 2 ) INFORMATION FOR SEQ ID NO:13:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:13:

Gln Gly Ile Ala
1

( 2 ) INFORMATION FOR SEQ ID NO:14:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:14:

Glu Gly Leu Arg
1

( 2 ) INFORMATION FOR SEQ ID NO:15:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:15:

Gly His Phe Arg
1

( 2 ) INFORMATION FOR SEQ ID NO:16:

( i ) SEQUENCE CHARACTERISTICS:
      ( A ) LENGTH: 4 amino acids
      ( B ) TYPE: amino acid
      ( C ) STRANDEDNESS:

(D) TOPOLOGY: linear (ii) MOLECULE TYPE: peptide (xi) SEQUENCE DESCRIPTION: SEQ ID NO:16:

Leu Glu Val Met
1

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product="Nle"

(xi) SEQUENCE DESCRIPTION: SEQ ID NO:17:

Leu Glu Val Xaa
1

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Ile His Ile Gln
1

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

Ala Asn Tyr Asn
1

(2) INFORMATION FOR SEQ ID NO:20:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Ala Gly Glu Arg
1

(2) INFORMATION FOR SEQ ID NO:21:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:21:

Ala Gly Phe Ala
1

( 2 ) INFORMATION FOR SEQ ID NO:22:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:22:

Gln Gly Leu Ala
1

( 2 ) INFORMATION FOR SEQ ID NO:23:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:23:

Ala Gln Phe Val
1

( 2 ) INFORMATION FOR SEQ ID NO:24:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:24:

Ala Gly Val Glu
1

( 2 ) INFORMATION FOR SEQ ID NO:25:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:25:

Phe Cys Met Leu
1

( 2 ) INFORMATION FOR SEQ ID NO:26:

( i ) SEQUENCE CHARACTERISTICS:
: ( A ) LENGTH: 4 amino acids
: ( B ) TYPE: amino acid
: ( C ) STRANDEDNESS:
: ( D ) TOPOLOGY: linear ( i i ) MOLECULE TYPE: peptide ( i x ) FEATURE:
: ( A ) NAME/KEY: Modified-site
: ( B ) LOCATION: 3
: ( D ) OTHER INFORMATION: /product="Nle"

( x i ) SEQUENCE DESCRIPTION: SEQ ID NO:26:

Phe Cys Xaa Leu
1

( 2 ) INFORMATION FOR SEQ ID NO:27:

: ( i ) SEQUENCE CHARACTERISTICS:
: : ( A ) LENGTH: 4 amino acids
: : ( B ) TYPE: amino acid
: : ( C ) STRANDEDNESS:
: : ( D ) TOPOLOGY: linear : ( i i ) MOLECULE TYPE: peptide : ( x i ) SEQUENCE DESCRIPTION: SEQ ID NO:27:

His Phe Leu Arg
1

( 2 ) INFORMATION FOR SEQ ID NO:28:

: ( i ) SEQUENCE CHARACTERISTICS:
: : ( A ) LENGTH: 4 amino acids
: : ( B ) TYPE: amino acid
: : ( C ) STRANDEDNESS:
: : ( D ) TOPOLOGY: linear : ( i i ) MOLECULE TYPE: peptide : ( x i ) SEQUENCE DESCRIPTION: SEQ ID NO:28:

Gly Leu Phe Ser
1

( 2 ) INFORMATION FOR SEQ ID NO:29:

: ( i ) SEQUENCE CHARACTERISTICS:
: : ( A ) LENGTH: 4 amino acids
: : ( B ) TYPE: amino acid
: : ( C ) STRANDEDNESS:
: : ( D ) TOPOLOGY: linear : ( i i ) MOLECULE TYPE: peptide : ( x i ) SEQUENCE DESCRIPTION: SEQ ID NO:29:

Leu Ala Phe Leu
1

( 2 ) INFORMATION FOR SEQ ID NO:30:

: ( i ) SEQUENCE CHARACTERISTICS:
: : ( A ) LENGTH: 4 amino acids
: : ( B ) TYPE: amino acid
: : ( C ) STRANDEDNESS:
: : ( D ) TOPOLOGY: linear : ( i i ) MOLECULE TYPE: peptide : ( x i ) SEQUENCE DESCRIPTION: SEQ ID NO:30:

His Phe Val Arg
1

(2) INFORMATION FOR SEQ ID NO:31:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Leu Leu His Asn
1

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Gln Tyr Thr Tyr
1

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

Gln Tyr Ser Asn
1

(2) INFORMATION FOR SEQ ID NO:34:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

Ile Tyr Ser Gln
1

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Asp Gly Ser Gly Gly Gly Glu Asp Glu Lys
 1           5                  10
```

(2) INFORMATION FOR SEQ ID NO:36:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

```
Lys Glu Asp Gly Gly Asp Lys
 1           5
```

(2) INFORMATION FOR SEQ ID NO:37:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

```
Asp Gly Ser Gly Glu Asp Glu Lys
 1           5
```

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
Asp Gly Gly Gly Lys Lys
 1           5
```

(2) INFORMATION FOR SEQ ID NO:39:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

```
Lys Glu Asp Glu Gly Ser Gly Asp Lys
 1           5
```

(2) INFORMATION FOR SEQ ID NO:40:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site ( B ) LOCATION: 1
        ( D ) OTHER INFORMATION: /product="OTHER"
            / note= "Xaa = donor fluorophore
            5'- carboxytetramethylrhodamine (C2211)
            linked to the alpha-amino group of Asp"

( i x ) FEATURE:
        ( A ) NAME/KEY: Modified-site
        ( B ) LOCATION: 5
        ( D ) OTHER INFORMATION: /product="Nle"

( i x ) FEATURE:
        ( A ) NAME/KEY: Modified-site
        ( B ) LOCATION: 9
        ( D ) OTHER INFORMATION: /product="OTHER"
            / note= "Xaa = acceptor fluorophore
            rhodamine X acetamide (R492) linked to
            the sulfhydryl group of Cys"

( x i ) SEQUENCE DESCRIPTION: SEQ ID NO:40:

Xaa  Ala  Ile  Pro  Xaa  Ser  Ile  Pro  Xaa
    1                    5

( 2 ) INFORMATION FOR SEQ ID NO:41:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:41:

Ile  Pro  Met  Ser  Ile
    1                    5

( 2 ) INFORMATION FOR SEQ ID NO:42:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /product="Nle"

( x i ) SEQUENCE DESCRIPTION: SEQ ID NO:42:

Asp  Ala  Ile  Pro  Xaa  Ser  Ile  Pro  Cys
    1                    5

( 2 ) INFORMATION FOR SEQ ID NO:43:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:43:

Asp  Ala  Ile  Pro  Met  Ser  Ile  Pro  Cys
    1                    5

( 2 ) INFORMATION FOR SEQ ID NO:44:

( i ) SEQUENCE CHARACTERISTICS:
   ( A ) LENGTH: 11 amino acids
   ( B ) TYPE: amino acid
   ( C ) STRANDEDNESS:
   ( D ) TOPOLOGY: linear ( i i ) MOLECULE TYPE: peptide ( i x ) FEATURE:
   ( A ) NAME/KEY: Modified-site
   ( B ) LOCATION: 1
   ( D ) OTHER INFORMATION: /product="OTHER"
       / note= "Xaa = a mixture of fluorophores
       5- and 6- carboxytetramethylrhodamine
   ( C 1 1 7 1 ) linked to the alpha-amino group
       of Asp"

( i x ) FEATURE:
   ( A ) NAME/KEY: Modified-site
   ( B ) LOCATION: 5
   ( D ) OTHER INFORMATION: /product="Nle"

( i x ) FEATURE:
   ( A ) NAME/KEY: Modified-site
   ( B ) LOCATION: 9
   ( D ) OTHER INFORMATION: /product="OTHER"
       / note= "Xaa = a mixture of fluorophores
       5- and 6- carboxy-X-rhodamine (C1309)
       linked to the epsilon-amino group of
       Lys"

( x i ) SEQUENCE DESCRIPTION: SEQ ID NO:44:

Xaa Ala Ile Pro Xaa Ser Ile Pro Xaa Gly Tyr
1                 5                 10

( 2 ) INFORMATION FOR SEQ ID NO:45:

( i ) SEQUENCE CHARACTERISTICS:
   ( A ) LENGTH: 11 amino acids
   ( B ) TYPE: amino acid
   ( C ) STRANDEDNESS:
   ( D ) TOPOLOGY: linear ( i i ) MOLECULE TYPE: peptide ( i x ) FEATURE:
   ( A ) NAME/KEY: Modified-site
   ( B ) LOCATION: 1
   ( D ) OTHER INFORMATION: /product="OTHER"
       / note= "Xaa = a mixture of fluorophores
       5- and 6- carboxy-X-rhodamine (C1309)
       linked to the alpha-amino group of Asp"

( i x ) FEATURE:
   ( A ) NAME/KEY: Modified-site
   ( B ) LOCATION: 5
   ( D ) OTHER INFORMATION: /product="Nle"

( i x ) FEATURE:
   ( A ) NAME/KEY: Modified-site
   ( B ) LOCATION: 9
   ( D ) OTHER INFORMATION: /product="OTHER"
       / note= "Xaa = a mixture of fluorophores
       5- and 6- carboxytetramethylrhodamine
   ( C 1 1 7 1 ) linked to the epsilon-amino
       group of Lys"

( x i ) SEQUENCE DESCRIPTION: SEQ ID NO:45:

Xaa Ala Ile Pro Xaa Ser Ile Pro Xaa Gly Tyr
1                 5                 10

( 2 ) INFORMATION FOR SEQ ID NO:46:

( i ) SEQUENCE CHARACTERISTICS:
   ( A ) LENGTH: 11 amino acids
   ( B ) TYPE: amino acid (C) STRANDEDNESS:
            (D) TOPOLOGY: linear (i i) MOLECULE TYPE: peptide (i x) FEATURE:
            (A) NAME/KEY: Modified-site
            (B) LOCATION: 1
            (D) OTHER INFORMATION: /product="OTHER"
                    / note= "Xaa = a mixture of fluorophores
                    5- and 6- carboxytetramethylrhodamine
                    (C 1 1 7 1) linked to the alpha-amino group
                    of Asp"

(i x) FEATURE:
            (A) NAME/KEY: Modified-site
            (B) LOCATION: 5
            (D) OTHER INFORMATION: /product="Nle"

(i x) FEATURE:
            (A) NAME/KEY: Modified-site
            (B) LOCATION: 9
            (D) OTHER INFORMATION: /product="OTHER"
                    / note= "Xaa = a mixture of fluorophores
                    5- and 6- carboxytetramethylrhodamine
                    (C 1 1 7 1) linked to the epsilon-amino
                    group of Lys"

(x i) SEQUENCE DESCRIPTION: SEQ ID NO:46:

Xaa  Ala  Ile  Pro  Xaa  Ser  Ile  Pro  Xaa  Gly  Tyr
    1                  5                        10

(2) INFORMATION FOR SEQ ID NO:47:

(i) SEQUENCE CHARACTERISTICS:
            (A) LENGTH: 11 amino acids
            (B) TYPE: amino acid
            (C) STRANDEDNESS:
            (D) TOPOLOGY: linear (i i) MOLECULE TYPE: peptide (i x) FEATURE:
            (A) NAME/KEY: Modified-site
            (B) LOCATION: 5
            (D) OTHER INFORMATION: /product="Nle"

(i x) FEATURE:
            (A) NAME/KEY: Modified-site
            (B) LOCATION: 9
            (D) OTHER INFORMATION: /product="OTHER"
                    / note= "Xaa = a mixture of fluorophores
                    5- and 6- carboxy-X-rhodamine (C1309)
                    linked to the epsilon-amino group of
                    Lys"

(x i) SEQUENCE DESCRIPTION: SEQ ID NO:47:

Asp  Ala  Ile  Pro  Xaa  Ser  Ile  Pro  Xaa  Gly  Tyr
    1                  5                        10

(2) INFORMATION FOR SEQ ID NO:48:

(i) SEQUENCE CHARACTERISTICS:
            (A) LENGTH: 11 amino acids
            (B) TYPE: amino acid
            (C) STRANDEDNESS:
            (D) TOPOLOGY: linear (i i) MOLECULE TYPE: peptide (i x) FEATURE:
            (A) NAME/KEY: Modified-site
            (B) LOCATION: 1
            (D) OTHER INFORMATION: /product="OTHER"
                    / note= "Xaa = a mixture of fluorophores
                    5- and 6- carboxy-X-rhodamine (C1309)

linked to the alpha-amino group of Asp"

(ix) FEATURE:
 (A) NAME/KEY: Modified-site
 (B) LOCATION: 5
 (D) OTHER INFORMATION: /product="Nle"

(xi) SEQUENCE DESCRIPTION: SEQ ID NO:48:

```
Xaa Ala Ile Pro Xaa Ser Ile Pro Lys Gly Tyr
1               5                   10
```

(2) INFORMATION FOR SEQ ID NO:49:

(i) SEQUENCE CHARACTERISTICS:
  (A) LENGTH: 11 amino acids
  (B) TYPE: amino acid
  (C) STRANDEDNESS:
  (D) TOPOLOGY: linear (ii) MOLECULE TYPE: peptide (ix) FEATURE:
  (A) NAME/KEY: Modified-site
  (B) LOCATION: 5
  (D) OTHER INFORMATION: /product="Nle"

(ix) FEATURE:
  (A) NAME/KEY: Modified-site
  (B) LOCATION: 9
  (D) OTHER INFORMATION: /product="OTHER"
   / note= "Xaa = a mixture of fluorophores
   5- and 6- carboxytetramethylrhodamine
  (C 1 1 7 1) linked to the epsilon-amino
   group of Lys"

(xi) SEQUENCE DESCRIPTION: SEQ ID NO:49:

```
Asp Ala Ile Pro Xaa Ser Ile Pro Xaa Gly Tyr
1               5                   10
```

(2) INFORMATION FOR SEQ ID NO:50:

(i) SEQUENCE CHARACTERISTICS:
  (A) LENGTH: 11 amino acids
  (B) TYPE: amino acid
  (C) STRANDEDNESS:
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /product="OTHER"
   / note= "Xaa = a mixture of fluorophores
   5- and 6- carboxytetramethylrhodamine
  (C 1 1 7 1) linked to the alpha-amino group
   of Asp"

(ix) FEATURE:
  (A) NAME/KEY: Modified-site
  (B) LOCATION: 5
  (D) OTHER INFORMATION: /product="Nle"

(xi) SEQUENCE DESCRIPTION: SEQ ID NO:50:

```
Xaa Ala Ile Pro Xaa Ser Ile Pro Lys Gly Tyr
1               5                   10
```

(2) INFORMATION FOR SEQ ID NO:51:

(i) SEQUENCE CHARACTERISTICS:
  (A) LENGTH: 11 amino acids
  (B) TYPE: amino acid
  (C) STRANDEDNESS:
  (D) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /product="OTHER"
       / note= "Xaa = fluorescein linked to the
       alpha-amino group of Asp"

( i x ) FEATURE:
    ( A ) NAME/KEY: Modified-site
    ( B ) LOCATION: 5
    ( D ) OTHER INFORMATION: /product="Nle"

( i x ) FEATURE:
    ( A ) NAME/KEY: Modified-site
    ( B ) LOCATION: 9
    ( D ) OTHER INFORMATION: /product="OTHER"
       / note= "Xaa = fluorescien linked to the
       epsilon- amino group of Lys"

( x i ) SEQUENCE DESCRIPTION: SEQ ID NO:51:

Xaa Ala Ile Pro Xaa Ser Ile Pro Xaa Gly Tyr
1                   5                   10

( 2 ) INFORMATION FOR SEQ ID NO:52:

( i ) SEQUENCE CHARACTERISTICS:
    ( A ) LENGTH: 11 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /product="OTHER"
       / note= "Xaa = a mixture of fluorophores
       5- and 6- carboxy-X-rhodamine (C1309)
       linked to the alpha-amino group of Asp"

( i x ) FEATURE:
    ( A ) NAME/KEY: Modified-site
    ( B ) LOCATION: 5
    ( D ) OTHER INFORMATION: /product="Nle"

( i x ) FEATURE:
    ( A ) NAME/KEY: Modified-site
    ( B ) LOCATION: 9
    ( D ) OTHER INFORMATION: /product="OTHER"
       / note= "Xaa = a mixture of fluorophores
       5- and 6- carboxy-X-rhodamine (C1309)
       linked to the epsilon-amino group of
       Lys"

( x i ) SEQUENCE DESCRIPTION: SEQ ID NO:52:

Xaa Ala Ile Pro Xaa Ser Ile Pro Xaa Gly Tyr
1                   5                   10

( 2 ) INFORMATION FOR SEQ ID NO:53:

( i ) SEQUENCE CHARACTERISTICS:
    ( A ) LENGTH: 12 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /product="OTHER"

/ note= "Xaa = a mixture of fluorophores
5- and 6- carboxytetramethylrhodamine
( C 1 1 7 1 ) linked to the epsilon-amino
group of Lys"

( i x ) FEATURE:
( A ) NAME/KEY: Modified-site
( B ) LOCATION: 6
( D ) OTHER INFORMATION: /product="Nle"

( i x ) FEATURE:
( A ) NAME/KEY: Modified-site
( B ) LOCATION: 10
( D ) OTHER INFORMATION: /product="OTHER"
/ note= "Xaa = a mixture of fluorophores
5- and 6- carboxy-X-rhodamine (C1309)
linked to the epsilon-amino group of
Lys"

( x i ) SEQUENCE DESCRIPTION: SEQ ID NO:53:

Xaa Asp Ala Ile Pro Xaa Ser Ile Pro Xaa Gly Tyr
1               5                   10

( 2 ) INFORMATION FOR SEQ ID NO:54:

( i ) SEQUENCE CHARACTERISTICS:
( A ) LENGTH: 12 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /product="OTHER"
/ note= "Xaa = a mixture of fluorophores
5- and 6- carboxytetramethylrhodamine
( C 1 1 7 1 ) linked to the epsilon-amino
group of Lys"

( i x ) FEATURE:
( A ) NAME/KEY: Modified-site
( B ) LOCATION: 6
( D ) OTHER INFORMATION: /product="Nle"

( i x ) FEATURE:
( A ) NAME/KEY: Modified-site
( B ) LOCATION: 10
( D ) OTHER INFORMATION: /product="OTHER"
/ note= "Xaa = a mixture of fluorophores
5- and 6- carboxytetramethylrhodamine
( C 1 1 7 1 ) linked to the epsilon-amino
group of Lys"

( x i ) SEQUENCE DESCRIPTION: SEQ ID NO:54:

Xaa Asp Ala Ile Pro Xaa Ser Ile Pro Xaa Gly Tyr
1               5                   10

( 2 ) INFORMATION FOR SEQ ID NO:55:

( i ) SEQUENCE CHARACTERISTICS:
( A ) LENGTH: 12 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /product="OTHER"
/ note= "Xaa = fluorophore 1 linked to
the alpha- amino group of Asp"

```
( i x ) FEATURE:
        ( A ) NAME/KEY: Modified-site
        ( B ) LOCATION: 6
        ( D ) OTHER INFORMATION: /product="Nle"

( i x ) FEATURE:
        ( A ) NAME/KEY: Modified-site
        ( B ) LOCATION: 10
        ( D ) OTHER INFORMATION: /product="OTHER"
                / note= "Xaa = fluorophore 2 linked to
                the epsilon- amino group of Lys"

( x i ) SEQUENCE DESCRIPTION: SEQ ID NO:55:

Xaa  Asp  Ala  Ile  Pro  Xaa  Ser  Ile  Pro  Xaa  Gly  Tyr
    1                   5                        10

( 2 ) INFORMATION FOR SEQ ID NO:56:

( i ) SEQUENCE CHARACTERISTICS:
            ( A ) LENGTH: 5 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:56:

Lys  Lys  Gly  Gly  Gly
    1              5
```